United States Patent
Earthman et al.

(10) Patent No.: US 12,082,940 B1
(45) Date of Patent: Sep. 10, 2024

(54) DETERMINATION OF STRUCTURAL CHARACTERISTICS OF AN OBJECT

(71) Applicant: Perimetrics, LLC

(72) Inventors: James C. Earthman, Irvine, CA (US); Cherilyn G. Sheets, Newport Beach, CA (US); Dennis A. Quan, Jr., Cary, NC (US)

(73) Assignee: Perimetrics, Inc., Redmond, WA (US)

( * ) Notice: Subject to any disclaimer, the term of this patent is extended or adjusted under 35 U.S.C. 154(b) by 733 days.

(21) Appl. No.: 16/731,020

(22) Filed: Dec. 30, 2019

Related U.S. Application Data

(60) Provisional application No. 62/786,494, filed on Dec. 30, 2018.

(51) Int. Cl.
| | |
|---|---|
| *A61B 5/00* | (2006.01) |
| *A61B 9/00* | (2006.01) |
| *A61C 9/00* | (2006.01) |
| *G06F 11/22* | (2006.01) |
| *G06F 30/10* | (2020.01) |
| *G06F 30/20* | (2020.01) |
| *G16H 50/50* | (2018.01) |

(52) U.S. Cl.
CPC .............. *A61B 5/4547* (2013.01); *A61B 9/00* (2013.01); *A61C 9/0046* (2013.01); *A61C 9/0053* (2013.01); *G06F 11/2247* (2013.01); *G06F 11/2263* (2013.01); *G06F 11/2268* (2013.01); *G06F 11/2289* (2013.01); *G06F 30/10* (2020.01); *G06F 30/20* (2020.01); *G16H 50/50* (2018.01)

(58) Field of Classification Search
CPC ........... A61B 9/00; G06F 30/10; G06F 30/20; G16H 50/50
See application file for complete search history.

(56) References Cited

U.S. PATENT DOCUMENTS

| | | | | |
|---|---|---|---|---|
| 6,120,466 | A | * | 9/2000 | Earthman ................ A61B 9/00 600/553 |
| 2013/0174639 | A1 | * | 7/2013 | Earthman ............. A61B 5/1111 367/189 |

OTHER PUBLICATIONS

Sheets 2016 (Sheets, C. G., Wu, J. C., Rashad, S., Phelan, M., & Earthman, J. C. (2016). In vivo study of the effectiveness of quantitative percussion diagnostics as an indicator of the level of the structural pathology of teeth. The Journal of Prosthetic Dentistry, 116(2), 191-199.) (Year: 2016).*

(Continued)

*Primary Examiner* — Bijan Mapar
(74) *Attorney, Agent, or Firm* — Quan & Associates; Nancy Quan; Christopher Quan

(57) ABSTRACT

The present invention relates generally to a system and method for measuring the structural characteristics of an object. The object is subjected to an energy application processes and provides an objective, quantitative measurement of structural characteristics of an object. The system may include a device, for example, a percussion instrument, capable of being reproducibly placed against the object undergoing such measurement for reproducible positioning. The invention provides for a system and methods for analyzing measured characteristics to identify issues and pathologies in the object, such as a tooth, and to recommend follow-up courses of action.

20 Claims, 7 Drawing Sheets

(56) References Cited

OTHER PUBLICATIONS

Sheets 2013 (Sheets CG, Hui DD, Bajaj V, Earthman JC. Quantitative percussion diagnostics and bone density analysis of the implant-bone interface in a pre- and postmortem human subject. Int J Oral Maxillofac Implants. Nov.-Dec. 2013;28(6):1581-8. doi: 10.11607/jomi.3037. PMID: 24278927 (Year: 2013).*

Scanlan, J., Li, F. F., Umnova, O., Rakoczy, G., Lovey, N., & Scanlan, P. (2018). Detection of osteoporosis from percussion responses using an electronic stethoscope and machine learning. Bioengineering, 5(4), 107. (Year: 2018).*

* cited by examiner

DETERMINATION OF STRUCTURAL CHARACTERISTICS OF AN OBJECT

CROSS-REFERENCE TO RELATED APPLICATIONS

This application claims the benefit and priority of the following U.S. Provisional Patent Application Ser. No. 62/786,494, filed Dec. 30, 2018, entitled "DETERMINATION OF STRUCTURAL CHARACTERISTICS OF AN OBJECT", the contents of all of the foregoing applications are hereby incorporated by reference in their entireties.

COPYRIGHT NOTICE

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

FIELD OF THE INVENTION

The present invention relates to a system and method for measuring structural characteristics of an object in a non-invasive manner and/or a non-destructive manner. The system may include an information acquisition module for acquiring information of physical objects, which may be anatomical or non-anatomical. The information acquired from physical objects may include test data that may be from the same object, but tested at different times, or from different objects that may or may not be related to one another.

BACKGROUND OF THE INVENTION

Every object, for example, any structure, either anatomical or non-anatomical including industrial or mechanical, exhibits some kind of structural characteristics that may change with time when the structures are being used in any manner, including those that are merely left standing in place in the environment. For changes that are easily discernable visually or revealed through simple testing, measuring the changes can be easily done. However, when such changes are not easily discernable visually or revealed through simple testing, more complicated testing is needed. Testing to find out such changes are important for the health and longevity of the structure, because such changes may eventually develop into some forms of defects that are not repairable over time if left unchecked or untreated. To determine the characteristics of the structure, a number of ways maybe used, but a majority of tests are likely destructive or invasive if such changes are internal.

Dental systems, either natural teeth or implants, may develop defects over time. Some defects require a dental restorative procedure to be performed. Such procedures can be invasive and expensive and incur long recovery times, especially if such defects are not easily discernable until they have developed into more discernable ones that may be severe. There is a significant need for technologies that can quickly validate and pinpoint the kind of issues present and their locations when before the issue becomes severe and/or prior to a disruptive procedure so as to reduce the risk of procedures being performed ineffectively or unnecessarily.

SUMMARY OF THE INVENTION

The present invention relates to a system and method for measuring structural characteristics of an object in a non-invasive manner and/or a non-destructive manner. The system may include an information acquisition module for acquiring information of physical objects, which may be anatomical or non-anatomical. The information acquired from physical objects may include test data that may be from the same object, but tested at different times, or from different objects that may or may not be related to one another. Surprisingly, the inventors have found that when compiling a multitude of test results collected from the same or different test objects that have been properly annotated, a "transformation function" that predicts structural characteristics and that is based on a predictive model may be generated from which a combination of no more than two relevant factors of the test results may be useful not only to predict structural characteristics of the object the collected test results come from, but to quickly predict, with one test, the same test that was used to generate the model, without further annotation and/or validation, the kind of issues present in related and may be unrelated objects, the issues that are not discernable visually or from, for example, radiographs when the object is a tooth. Further, the predictive model may also be useful in aiding in determining proper measures for further testing, proper corrective measures to continue monitoring and/or restore the object to substantially issue free stage. In addition, the predictive model may in some instances provide more insight into the structural characteristics than using the test results of the object alone.

In some embodiments, the system's transformation function identifies structural characteristics when one or more of the relevant factors fall into one or more characteristic ranges. The bounds of the characteristic ranges are bounded by one or more threshold value settings that can be tuned and adjusted.

The system and method for predicting at least one structural characteristic of an object using a predictive model may include a compilation of test results from a multitude of objects, each of the test results being generated by a device to be further described below, having a housing with an open end and a longitudinal axis including an energy application tool mounted inside the housing for movement between a resting and an active configuration; a sleeve portion protruding from the open end of the housing for a distance and having an object contacting portion at its open end adapted for resting the device on at least a portion of the object being tested; and a drive mechanism supported inside the housing adapted for activating the energy application tool to impact the object when the object contacting portion of the sleeve portion is resting on at least a portion of the object and for measuring a response after impact and generating a response versus time curve.

In some embodiments, the response versus time curve may be annotated and validated by a technician as having zero or more structural characteristics. A computer may be coupled to the device for capturing the response versus time curve and associated annotation to generate the predictive model. The combination of no more than two relevant factors (transformation function) from the predictive model may be used to predict at least one structural characteristic of a newly tested object using the same device as above along with the transformation function without the need for annotation and/or validation.

In some embodiments, the measuring of a new object and annotation of the produced measurement may cause at least one of the threshold value settings to be adjusted. In some exemplary embodiments, the threshold value settings are adjusted using a statistical model, such as logistic regression, based on all of the measurements and annotations collected up to that point.

In some exemplary embodiments, the threshold value settings for one instance of the system are set based on values previously adjusted in another instance of the system that has processed at least one prior measurement and annotation.

The predictive model may include information collected from other tests not generated by the device described above. For example, for an anatomical object, other tests results may include computer modeling, radiography, transillumination, disassembling, or even examinations after extraction, or combinations thereof.

The present invention further relates to a computerized system and method for automatically determining structural characteristics of an object in a non-invasive manner and/or a non-destructive manner after an operator performs the test using any of the systems described above and below. The computer system may be implemented with programs to automatically determine the relevant factors and comparing the data with the predictive model to arrive at the measured structural characteristics of the object.

The above predictive model and test procedure used to generate results may be loaded into a test device equipped with the features of the device above so that the test device may automatically instruct an operator to test a new object and after the test procedure is carried out, to automatically generate a transformation function as noted above, and using the generated transformation function to predict at least one structural characteristic of the new object without further operator participation.

The system and method may include a device having an energy application tool capable of applying energy to an object to generate a response, for example, a percussive response that may reveal the structural characteristics of the object without substantially affecting the existing structural characteristics of the object. The energy application tool may be programmed to impact an object a certain number of times per minute at substantially the same speed for a certain time interval during testing. The system may measure, for a time interval, a percussive response such as energy reflected from the object as a result of the energy application, for example, by tapping or applying energy, or the deceleration information of the energy application tool, namely energy return. The response may be fed to a computer and the information is recorded or compiled for analysis by the system, which may include creating a percussive response profile, for example, an energy return curve or energy return graph (ERG) as a time-energy profile, frequency-energy profile, based on the energy reflected from the object during the time interval, and/or evaluating the, for example, percussive response profile, for example, a time-energy profile, to determine the structural characteristics of the object, for example, vibration damping capacities; acoustic damping capacities; defects including inherent defects in, for example, the bone or the material that made up the object; cracks, micro-cracks, fractures, microfractures; loss of cement seal; cement failure; bond failure; microleakage; lesions; decay; structural integrity in general or structural stability in general.

The combinations of relevant factors involved in the present invention are loss coefficient or mobility and normal fit error (NFE) or damage or stability based on the ERG versus time curve shape. Loss coefficient in general is an indication of the overall ability in damping capability in the object or structure being tested. In the percussion process, it is based on the maximum energy return or percussion force squared that are measured with the measuring or sensing mechanism coupled to the energy application tool, for example, the percussion rod, as discussed below. The normal fit error (NFE) or damage or instability, is the overall error (difference) between an ideal curve (generated by a defect free object) and the actual test data. The inventors have found that the severity of structural pathology, for example, damage, increases as this error increases. All response curves are normalized to a maximum of one prior to determining NFE and thus it is not directly related to loss coefficient.

For an anatomical object, the structural characteristics of, such as a tooth structure, a natural tooth, a natural tooth that has a fracture due to wear or trauma, a natural tooth that has become at least partially abscessed, or a natural tooth that has undergone bone loss or a bone augmentation procedure, a prosthetic dental implant structure, a dental structure, an orthopedic structure or an orthopedic implant, such characteristics may indicate the health of the object, or the health of the underlying foundation to which the object may be anchored or attached may be tested to generate a loss coefficient and an NFE factor. The test results may be related to the health of the object and/or the underlying foundation. The health of the object or foundation may also be correlated to densities or bone densities or a level of osseointegration; any defects, inherent or otherwise; or cracks, fractures, microfractures, microcracks; loss of cement seal; cement failure; bond failure; microleakage; lesion; or decay that may have weakened the structure in a way that creates micro movement within the structure. For objects in general, for example, polymeric composite structures including honeycombs or layered honeycombs or metallic composite structures; planes, automobiles, ships, bridges, buildings, industrial structures including, but not limited to power generation facilities, arch structures, or other similar physical structures; such measurements may also be correlated to any structural integrity, or structural stability, such as defects or cracks, even hairline fractures or microcracks, and so on.

Additionally, changes in the structure of the tooth or any foundation a mechanical structure is attached or anchored to that reduce its ability to dissipate the mechanical energy associated with an impact force, and thus reduce overall structural stability of the, for example, tooth, can be detected by evaluation of the energy return data as compared to an ideal non-damaged sample. In addition, as noted above, the present invention also contributes to the accuracy of the location of detection of defects, cracks, micro-cracks, fractures, microfracture, leakage, lesions, loss of cement seal; microleakage; decay; structural integrity in cement failure; bond failure; general or structural stability in general.

As mentioned above, each test may generate one profile and the profile generated may be complicated. Time and energy are spent also to validate the interpretation of the test results using other methods, such as radiographs, transillumination and if the profiles predict serious defects, more destructive methods such as disassembly or even extraction in terminal situations. The present inventors have found a way to compile validated test information from the profiles into a predictive model for predicting whether defects or abnormalities may or may not be present in any object that may or may not have not been tested, using a combination of not more than the two relevant factors noted above. Thus, instead of having to go through complicated annotation and/or validation steps, which may or may not correctly validate the test without costly and time consuming process, each time a test is performed, only two factors from the percussion test results of the new object need be generated for the model to predict the absence or presence of a defect, or locate a defect and recommend a rehabilitation procedure. The model created using validated results may generate a form of decision tree that may be used to predict the structural characteristics of an object with a simple non-invasive percussion test, without having to perform the actual validation testing, which may be complicated, in addition to being sometimes invasive and/or destructive.

In general, when a percussion device is used, the Normal Fit Error (NFE) may be determined as follows:
1. The Defect Severity Quotient (DSQ) is equal to NFE× 1000.
2. The Damage (D) is given by D=27×ln(DSQ)−61, where ln is the natural logarithm.

As noted above, the force may be determined by a sensor coupled to the energy application tool. The energy return data generated in a test is normalized before fitting to these data is performed. In other words, for an energy application tool that is a tapping rod, the equation to be fitted is for $E_r/E_{rmax}$ instead of just the energy return, $E_r$, which characterizes the elastic energy of this force measurement. For example, $E_r$ is defined as $E_r=F^2/2K$, where F is the resultant percussion force and K is the stiffness of the energy application tool, for example, the tapping rod assembly. The normalized energy return, variation with tie for a defect-free calibration sample could be expressed in the form:

$$\overline{E}_r = \beta \sin^2(\gamma t) \exp\left[-\frac{(t-\phi)^2}{\psi}\right]$$

where t is time and $\beta$, $\gamma$, $\phi$, and $\psi$ are parameters that are determined via a nonlinear regression fit to measured data. The NFE is equal to the cumulative error between the normalized measured data and a nonlinear regression fit of the equation above to the normalized measured data. Thus, the NFE represents that overall difference between the shape of an ideal energy return response for a defect-free sample and that for the measured data.

In general, the loss coefficient may be derived from damping characteristics of an object, for example, tooth and implant. After application of kinetic energy to the object, the relative extent to which the object deforms inelastically and dampens elastic energy may be characterized as its loss coefficient, $\eta$, given by:

$\eta=D/2\pi U$ where D is the total energy dissipated (or lost) per unit volume and U is the elastic energy per unit volume. The stability index (SI) is equal to $Fp^2/Fc^2\times 100$ where Fp is the maximum percussion force measured by the sensor in the percussion rod for the sample tested and Fc is the maximum percussion force for a stiff calibration sample (e.g. aluminum alloy or stainless-steel block). Other calibration materials may also be used. The Mobility is equal to 100−SI. The combination of these two relevant factors are useful to predict structural characteristics of objects.

The percussion device useful in the present invention may come in different configurations, and the testing results produced from some configurations may generate better models than other configurations. In general, the device includes a percussion instrument, capable of being reproducibly placed directly on the object undergoing such measurement for reproducible measurements.

In some exemplary embodiments, the device used may include a handpiece having a housing having a longitudinal axis, with an open end and an energy application tool, for example, a tapping rod, or impact rod mounted inside the housing for axial movement along the longitudinal axis of the housing, or for oscillatory movement about the longitudinal axis of the housing. In one embodiment, the energy application tool, for example, a tapping rod, has a length with a retracted or resting form or configuration and an extended or active form or configuration, the retracted form being retracted from or substantially coextensive with the open end of the housing if the energy application tool is a tapping rod. The movement of the energy application tool, for example, a tapping rod, may be effected by a drive mechanism mounted inside the housing for driving the tapping rod axially within the housing between the aforementioned retracted position and extended position during operation. In the extended position, the free end of the tapping rod is capable of extending or protruding from the open end of the housing. In another embodiment, the resting configuration may be a form substantially parallel to the longitudinal axis of the housing, and the active configuration may be a form when the energy application tool, for example, a tapping rod, or impact rod mounted inside the housing forms an acute angle with the longitudinal axis of the housing, such as, for example, by rocking back and forth about a pivot point on the longitudinal axis. Thus, the energy application tool oscillates from the substantially parallel position to the longitudinal axis of the housing to a position making an acute angle with the longitudinal axis of the housing at a pivot point. The energy application tool may be held either horizontally or in other positions during measurement, and may have a tip portion that is substantially perpendicular to the major portion of the tool and maintains a constant length either at rest or at impact. The movement of the energy application tool, for example, a tapping rod, may be effected by a drive mechanism mounted inside the housing for driving the tapping rod from a substantially parallel position to the longitudinal axis of the housing to a position making an acute angle with the axis at a pivot point and back again, while the tip oscillates up and down in turn. The movement of the energy application tool, for example, a tapping rod, may be effected by a drive mechanism mounted inside the housing for driving the energy application tool.

The drive mechanism may be, for example, an electromagnetic mechanism, and may include an electromagnetic coil. In one embodiment, the drive mechanism may include a permanent magnet secured to the back end of the energy application tool, for example, the tapping rod, and the magnetic coil may lie axially behind this permanent magnet. Together with the back part of the handpiece housing and any electrical supply lines, the magnetic coil forms a structural unit which may be integrally operational and which may be, for example, connected to the remaining device by a suitable releasable connection, for example, a screw-type connection or a plug-type connection. This releasable connection may facilitate cleaning, repairing and others.

The energy application tool, such as the tapping rod, is located in the front part of the housing and the mounting mechanism for the tapping rod may include frictionless bearings. These bearings may include one or more axial openings so that the neighboring chambers formed by the housing and the tapping rod are in communication with one another for the exchange of air.

In one embodiment, the drive mechanism may include a measuring device, for example, a piezoelectric force sensor, located within the handpiece housing for coupling with the energy application tool, such as the tapping rod. The measuring device is adapted for measuring the deceleration of the tapping rod upon impact with an object during operation, or any vibration caused by the tapping rod on the specimen. The piezoelectric force sensor may detect changes in the properties of the object and may quantify objectively its internal characteristics. Data transmitted by the piezoelectric force sensor may be processed by a system program, to be discussed further below.

In some embodiments, the drive mechanism may include a linear variable differential transformer adapted for sensing and/or measuring the displacement of the energy application tool such as the tapping rod, before, during and after the application of energy. The linear variable differential transformer may be a non-contact linear displacement sensor. The sensor may utilize inductive technology and thus be capable of sensing any metal target. Also, the noncontact displacement measurement may allow a computer to determine velocity and acceleration just prior to impact so that the effects of gravity may be eliminated from the results.

Communication between the drive mechanism and the energy application may be wired or wireless.

The housing may include an object contacting portion, i.e., the open end of the housing. Located at the open end of the housing may be a sleeve, having an object contacting portion. In one embodiment, when a sleeve is present, the sleeve may attach and/or surround at least a length of the free end of the housing and protrudes from the housing at a distance substantially coextensive with the end of the tapping rod in its extended form if the tapping rod moves axially. Thus, the length of the sleeve may be dependent on the length of protrusion of the extended tapping rod desired. The free end of the sleeve may be placed against an object undergoing measurement. The object contacting portion of the housing or the sleeve, if a sleeve is present, may be placed directly in contact with the object during measurement, thus stabilizing the device on the object. Other features may be included to further stabilize the device and may also built in some repeatability of placement of the device on an object.

In some exemplary embodiments, the device may be as described in the above exemplary embodiment(s), except that the sleeve may include a tab protruding from at least a portion of its end so that when the open end of the sleeve is in contact with at least a portion of a surface of the object undergoing the measurement, the tab may be resting on a portion of the top of the object. The tab and the sleeve together assist in the repeatable positioning of the handpiece with respect to the object; thus results are more reproducible than without the tab. In rare situations, the tab may not protrude at all to allow testing at a lower position on the object. The tab may be substantially parallel to the longitudinal axis of the sleeve. In one aspect, the surface of the tab in contact with an object may be contoured, a concave or a convex surface, to be better positioned on the top of the object, for example, a tooth. In another aspect, the surface of the tab in contact with an object may be flat to accommodate the topography of the object, for example, a flat surface. In a further aspect, the surface of the tab in contact with an object have include a groove or groove to accommodate an object with uneven surfaces. In addition, the tab may be adapted for repetitively placed substantially at the same location on the top of the object every time. In one embodiment, the tab may be substantially parallel to the longitudinal axis of the sleeve.

On rare occasions, where the tab may interfere with a stable position on, for example a dental implant transfer abutment, a sleeve portion without a tab may be used for more stable placement lower on the abutment.

In some exemplary embodiments, the sleeve may include not only a tab, but also a feature component, for example, a ridge, protrusion or other feature substantially orthogonal to the surface of the tab on the side adapted for facing the surface of an object. For example, for teeth, the ridge or protrusion may nest between adjacent teeth or other orthogonal surface and may thus aid in preventing any substantial lateral or vertical movement of the tab across the surface of the object and/or further aid in repeatability. The tab may be of sufficient length or width, depending on the length or width of the top portion of the object so that the ridge or protrusion may be properly located during operation. Again, the tab and the feature also aid in the reproducible results than without the tab.

In some exemplary embodiments described above, the device may be of any form factor, including desktop or a portable device. A portable device may be in any form as long as it is portable, or it may be a handpiece with a longitudinal housing for housing the parts of the device as described above. The device, for example, a handpiece may be held at any angle to the horizontal during testing. The stabilization of the instrument effected by sleeve, the sleeve and a tab or a sleeve, a tab and/or component may minimize any jerky action by the operator that may confound the testing results, for example, any defects inherent in the bone structure or physical or industrial structure may be masked by jerky action of the tester. This type of defect detection is important because the location and extent of the defect may impact dramatically upon the stability of the implant or physical or industrial structures. Generally, when lesions are detected, for example, in an implant, such as a crestal or apical defect, the stability of the implant may be affected if both crestal and apical defect are present. In the past, there is no other way of gathering this type of information other than costly radiation intensive processes. With the present device, this type of information may be gathered, and may be done in an unobtrusive, non-invasive manner without radiation.

In some further exemplary embodiments, an inclinometer may be present, for example, as part of an electronic control system of any of the above described exemplary embodiments, which may trigger an audible warning when the device is outside of the angular range of operation; for example, for a tapping rod, it may trigger the warning when it is plus/minus approximately 45 degrees, more for example, 30 degrees from horizontal to return the device to the horizontal orientation.

In some exemplary embodiments, any of all of the exemplary embodiments described above may also include a force sensor, not for sensing or measuring the force exerted by the energy application tool on an object during testing, but for sensing and/or monitoring that a proper contact force is exerted by the sleeve portion on the object undergoing measurement. As mentioned above, during measurement, for example, the device may contact the object with the end of the sleeve portion. The contact force may vary depending on the operator. It is desirable that the force be consistently applied in a certain range and that range not be excessive, independent of the operator. A force sensor may be included in the device for sensing this force and may be accompanied by visual signal, voice or digital readout. This sensor may be employed also for assuring that proper alignment against the object during measurement is obtained. The sensor, for example a force sensor, may be in physical proximity and/or contact and/or coupled with at least a portion of the device other than the energy application tool; for example, it may be in physical proximity and/or contact and/or coupled with the housing and/or sleeve portion, if the open end of the sleeve portion includes an object contacting portion.

In general, the sensor may surround the energy application tool and not in physical contact with the tool. For example, the sensor maybe positioned such that the energy application tool, even a physical tool, may pass through it to impact the object undergoing measurement. The sensor may include strain gauges, piezoelectric elements, a sensing pad or any other sensor that may be capable of being sandwiched. The sensor, for example the force sensor, may be disposed anywhere inside the housing and be in physical proximity and/or contact and/or coupled with at least a portion of the device other than the energy application tool; for example, it may be in physical proximity and/or contact and/or coupled with the housing and/or sleeve portion, if the open end of the sleeve portion includes an object contacting portion, as noted above. In some embodiments of the invention, the sensor may include at least one strain gauge for sensing. The strain gauges may be attached or mounted to a cantilever between the device housing and the sleeve portion so that when the object contacting portion of the sleeve portion is pressed on the object it also deforms the cantilever which is measured by the strain gauge, thus providing a force measurement. In some embodiments, multiple strain gauges mounted to a single or to separate cantilevers may be utilized. The cantilever(s) may also, for example, be present on a separate component from the rest of the housing or sleeve portion, such as, for example, on a mounting device. In other embodiments of the invention, the sensor may include a sensing pad which may be positioned between a rigid surface and a sliding part so that when the pad is pressed or squeezed as the sliding part moves towards the rigid surface, the force is measured. According to one embodiment, the rigid surface may be, for example, a coil interface that holds the electromagnetic coil in the drive mechanism within the device housing of any of the above or below exemplary embodiments. The sliding part may be a force transfer sleeve-like component disposed inside the housing and coupled to the object contacting portion of the sleeve portion and adapted to slide inside the housing when a force is exerted by the object contacting portion of the sleeve portion on an object. In some embodiments, it may be disposed inside the sleeve portion. The sliding distance may be very small, for example, in the order of about (in millimeters or mm) 0.3 mm to about 1 mm, more for example about 0.5 mm. The sensing pad may include a layer structure, which may be generally referred to as a "Shunt Mode FSR" (force sensing resistor) that may change resistance depending on the force applied to the pad, to provide a force measurement. According to another embodiment, the force transfer sleeve-like component may be biased forward by a spring, so that when force is applied by the object contacting portion of the sleeve portion on the object, the force transfer sleeve-like portion may transfer the force against the spring. According to one aspect, the force sensing may be done by a linear position sensor, which would know, for example, that if the force transfer sleeve-like portion is at position X, a force of Y has to be applied to it (against the reaction force of the spring) to move it to that position. According to another aspect, the force sensing may be performed by an optical sensor, for optically sensing the position of the moving part, when it is pushed against a spring, In some embodiments of the invention, the relative position of the object contacting portion of the sleeve portion on the object may be determined by having one or more strain gauges which may be attached at one end to a moving part, for example, the force sensor sleeve-like component, and the other end to a static element, for example, the housing. In some embodiments of the invention, the device may include piezoelectric elements for directly measuring the force. In some embodiments of the invention, a hall effect sensor may be used to detect a change in the magnetic field when a magnet (attached to the moving element) is moving relative to the position of the sensor. In some embodiments of the invention, a capacitive linear encoder system, like that found in digital calipers may be used to measure the force.

In addition to monitoring and sensing the contact force exerted on the object by the operator when the sleeve portion contacts the object, the sensors may also be configured to activate the device when the correct amount of force is exerted on the object by the sleeve portion.

Though the sensor is not physically or mechanically coupled to the energy application tool, it may be in electronic communication with the energy application tool and may act as an on/off switch for the device or instrument, as noted above. For example, when a proper force is exerted on the object by the object contacting portion of the sleeve, it may trigger the activation mechanism of the device or instrument to activate the movement of the energy application tool to start a measurement. Thus, no external switches or push buttons are needed to activate the on and off of the system, as noted above. The indication of the proper force may be indicated by visible or audible signals.

The sleeve portion may be mounted onto a force transfer sleeve-like component, or force transfer member, that forms a permanent part of the front of the housing or protrudes from it, and shields the energy application tool, for example, the tapping rod, from damage when no sleeve portion is present, for example, the sleeve portion may form part of a disposable assembly, as discussed below. The force transfer sleeve-like component sits around the energy application tool, for example, a tapping rod; and may surround the energy application tool, is held at the front by the housing and mounts onto the front of the electromagnetic coil at the rear. The force transfer sleeve-like component may be adapted to slide a small amount, and in doing so, may act on a force sensor, for example, a force sensitive resistor, located between the back surface of the force transfer sleeve-like component and the coil mount. The energy application tool, for example the tapping rod may be triggered when the object contacting portion of the sleeve portion is pushed against an object undergoing measurement; for example, a tooth and a force may be detected. When a correct force within a certain range is detected, the instrument is turned on to start the measurement.

As mentioned above and in all the embodiments of the sensor, the sensor may be arranged to form a channel through which the energy application tool, such as a tapping rod, may pass through to impact the object undergoing measurement, i.e. surrounds the tapping rod.

If the device is oriented such that the axis of operation is greater than about 45 degrees, more for example, greater than about 30 degrees from horizontal when a push force is sensed on the object contacting portion of the sleeve portion, it may result in a warning sound being emitted by a speaker located on the device, such as the printed circuit board (PCB) within the device. In such circumstances, the percussion action will not begin until the device is returned to an acceptable angle. In some instances, if the percussion action has started when the above mentioned above-mentioned departure from the range is detected, the device may not actually stop operation, but may simply be sounding an alarm, so that corrections may be made.

In some exemplary embodiments, any of the above described exemplary embodiments, the system and method may also include a device capable of operating by holding the device at varying angles from the horizontal and modulating the energy application process to mimic a substantially horizontal position during measurement and may provide a system that may apply the optimal amount of energy to an object in all situations. The device may exert a substantially the same impact force on the object in various angles from the perpendicular direction of the object surface, as if the device is operating so that the direction of propagation is perpendicular to the surface of the object. Thus, whether the device is operating at about plus/minus 45 degrees, more for example, about plus/minus 30 degrees from the perpendicular direction with respect to the object surface, the device may still generate about the same amount of an equivalent impact force, for example, about 20-30 newtons, for optimal results.

The object may be subjected to an energy application process and the system is adapted for providing an objective, quantitative measurement of structural characteristics of the object after the energy application process. The drive mechanism varies the amount of energy applied to activate the energy application tool between the resting and active configurations based on the inclination to at least approximate the set amount of energy at inclinations other than horizontal. The drive mechanism may include an electromagnetic coil and may vary the amount of energy applied (e.g. varying voltage, current or both), may vary the coil drive times (varying the length of time the coil is energized or activated), may vary the coil delay times (varying the time between driving activities), may vary the number of coil energizations (i.e. varying the number of drive pulses applied), polarity of the coil and/or a combination thereof. These factors, including varying power, drive times, polarity and delay times may be managed through varying the firmware settings for power, drive time, number of drives, number of drive pulses, polarity and drive delay of the energizing of the coil for the desired results. Without wishing to be bound to any particular theory, it is surmised multiple variations may be employed to achieve the desired result and the firmware may be designed to select a particular solution or to select an optimal solution for certain instances. The system and method of the present invention may, such as increase flexibility of operation, for example, to adapt for reaching hard to reach objects, both anatomical and non-anatomical, to detect any abnormalities that may be present in an object to generate more reproducible measurements, and also to better be able to detect any abnormalities that may be present in an object. The device may include a housing with a hollow interior and an open end through which an energy application tool, including any tool capable of applying any types of energy to the object, for example, a tool capable of applying mechanical energy to the object, such as a tapping rod positioned inside the housing passes through to reach the object undergoing measurement, an electromagnetic energy of any frequency, for example, light, a sound wave such as acoustic energy.

For example, the system may include a device for performing a percussion action on an object. The device, having a housing with a hollow interior and an open end through which energy may be applied by an energy application tool, including any tool capable of applying any types of energy to the object including mechanical, sound or electromagnetic energy, may be positioned. In one embodiment, a tool capable of applying mechanical energy to the object, such as a tapping rod may be positioned inside the housing passes through to reach the object undergoing measurement. In another embodiment, an electromagnetic energy source of any frequency, such as light energy, for example, may be positioned inside the housing. In a further example, a sound energy source such as an ultrasonic transducer or any acoustic energy source, may be positioned inside the housing.

For any of the exemplary embodiments above, a system and method for measuring structural characteristics using an energy application tool may also include disposable features for aiding in eliminating or minimizing contamination of the object undergoing the measurement through transfer from the system or cross-contamination from previous objects undergoing the measurements, without interfering with the measurement or the capability of the system. The instrument includes a housing having a hollow interior with an open end and an energy application tool, for example, a tapping rod, or impact rod mounted inside the housing for movement inside the housing. The system provides a non-destructive method of measurement with some contact with the object undergoing such measurement without the need for wiping or autoclaving of the energy application tool, and at the same time without disposing of the energy application tool and/or the housing and whatever may be housed inside the housing of the instrument.

The disposable feature may include a covering for covering or enveloping a part of the system that may come into proximity or contact with the object undergoing the measurement without interfering with the sensitivity, reproducibility, if desired, or general operation of the instrument to any substantial degree.

The present invention may be applicable for testing various objects that are mechanical, as noted before. For a mechanical object, which may include, but not limited to polymeric composite structures including honeycombs or layered honeycombs or metallic composite structure; an airplane structure, an automobile, a ship, a bridge, a tunnel, a train, a building, industrial structures including, but not limited to power generation facilities, arch structures, or other similar physical structures, testing may also be carried out on stationary or a mobile object while moving. Thus, mechanical objects may also be undergoing testing when they are either stationary or moving, which may give particular insight into the object under actual working conditions. For moving objects, such as a train, the testing may be performed over many different spots. This may be performed using one energy application tool, over a plurality of spots on the object, to obtain an average condition of the object in general or be performed on the same spot using many separate tools or devices to obtain an average result on the same spot. For performing measurement on the same spot using many energy application tools, the devices or tools may be positioned, for example, in succession along the path of the moving object over a distance, for example, an array of tapping rod impacting the object, and by controlling the spacing between the tools or devices one may be able to match the speed of the moving object, for example a train, to the spacing of the application of energy on the same spot of the object for obtaining an average value for the spot. In this example, measurements may be performed under actual operating conditions. In one embodiment, the array of devices may be a line array, either vertical or horizontal arrays, or a curve array. In another aspect, the array may be arranged in a two-dimensional array, planar or curvilinear.

In embodiments where the object is large, measurement at different locations of the object, for example, impacting at a plurality of portions of the object may allow better evaluation of the structural properties that are better representations of the object.

The system and method of any of the above embodiments may also be useful in predicting a future course of action for the object having a certain predicted structural characteristic. The future course of action may include continuing monitoring, or further testing. As the predicted structural characteristics may vary with different test objects, so would any predictive course of action.

The predictive model as described above may be further aided through a program logic module ("Training") executing a training cycle for training a machine learning algorithm on a ground truth dataset including stored device measurements and expert annotations to create a transformation function.

The present invention together with the above and other advantages may best be understood in conjunction with the following detailed description of the aspects, embodiments and examples of the invention and as illustrated in the drawings. The following description, while indicating various aspects, embodiments and examples of the invention and numerous specific details thereof, is given by way of illustration and not of limitation. Many substitutions, modifications, additions or rearrangements may be made within the scope of the invention, and the invention includes all such substitutions, modifications, additions or rearrangements.

DETAILED DESCRIPTION OF THE INVENTION

Figure 1:
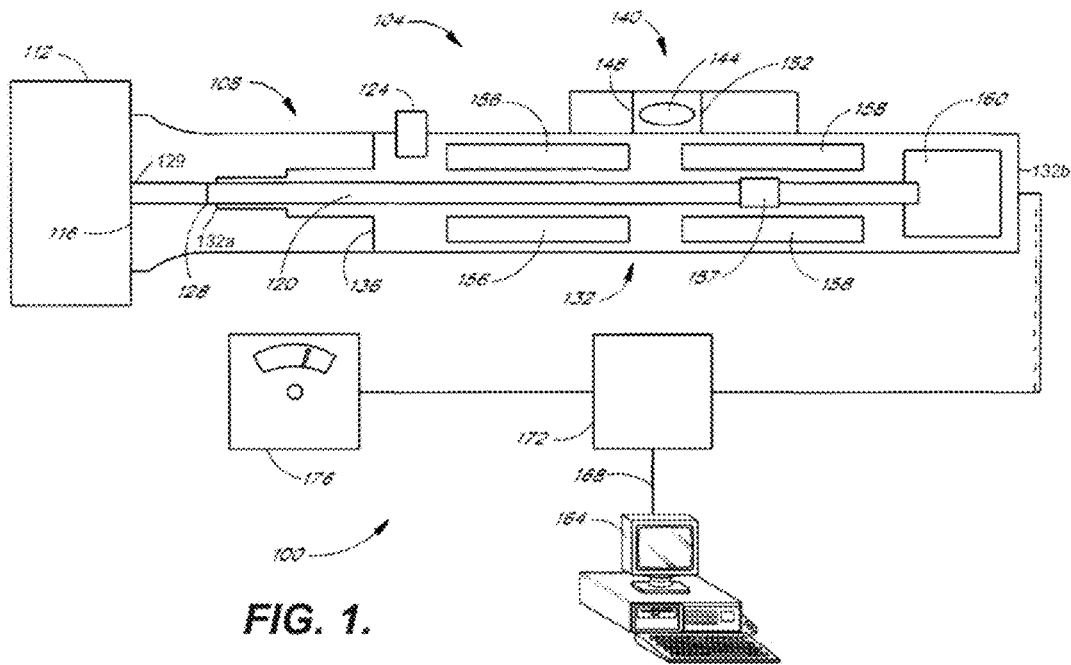
FIGS. 1, 2, 3, 4 and 4a illustrate block diagrams of measurement devices of the present invention.

The detailed description set forth below is intended as a description of some of the exemplified systems, devices and methods provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any systems, methods, devices and materials similar or equivalent to those described herein may be used in the practice or testing of the invention, some of the exemplified systems, methods, devices and materials are now described.

All publications mentioned herein are incorporated herein by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention relates to a system and method for measuring structural characteristics of an object in a non-invasive manner and/or a non-destructive manner using a predictive model generated from a multitude of test results that may be from the same object, but at different times, or from different objects that may or may not be related to one another, also at various times with a combination of no more than two relevant factors of the test results to predict structural characteristics not only of the object the collected test results come from, but to quickly predict, with one test, the same test from other test used to generate the model, the kind of issues present in related and may be unrelated objects, the issues that are not discernable visually or from, for example, other relatively non-invasive methods. The predictive model may also include information collected from other tests not generated by the device described herein. For example, for an anatomical object, other tests results may include computer modeling, radiography, transillumination, disassembling, or even examinations after extraction, or combinations thereof.

In some exemplary embodiments, a system for predicting at least one structural characteristic of an object using a predictive model, may include a compilation of test results from a multitude of objects, each of the test results being generated by a device having a housing with an open end and a longitudinal axis with an energy application tool mounted inside the housing for movement is disclosed. The energy application tool may include a resting and an active configuration. The housing may include an object contacting portion at its open end, or a sleeve may be included and may protrude from the open end of the housing for a distance and having an object contacting portion at its open end adapted for resting said device on at least a portion of said object. A drive mechanism supported inside the housing may be adapted for activating the energy application tool to impact an object when the object contacting portion of the housing or the sleeve is resting on at least a portion of the object and for measuring a response after impact and generating a response versus time curve, said response versus time curve having been annotated and validated. A computer may be coupled to the device adapted for capturing any of the responses, the response versus time curve and the annotation and validation to generate a predictive model. A transformation function including a combination no more than two relevant factors from the predictive model may be adapted for predicting at least one structural characteristic of a newly tested object using the above and below described device with said transformation function without the need for further annotation and validation.

In some exemplary embodiments, a computerized method for automatically determining structural characteristics of an object in a non-invasive manner and/or a non-destructive manner, including creating a predictive modeling by compiling test results from a multitude of objects, each of the test results being generated by a test procedure using a device described above and below, each having an energy application tool capable of applying energy to an object to generate a measurement to create a response versus time curve is disclosed. The response versus time curve may be annotated and validated and the response versus time curve and the annotation and validation may be complied to create said predictive model; The model and the test procedure may be loaded into a test device equipped similarly as the device described above. An operator is instructed to test a new object by using the above and below described test device on the new object to automatically generate a transformation function including a combination no more than two relevant factors from the model, and applying the transformation function to predict at least one structural characteristic of the new object without operator participation, or any further annotation or validation.

The present invention also includes a method for predicting at least one structural characteristic of an object using a predictive model, including generating test results from a multitude of objects. The test results may be generated using a device having an energy application tool capable of applying energy to an object to generate measurement to create a response versus time curve, and annotating and validating the response versus time curve. A computer may be coupled to the device for capturing the response versus time curve and the annotation and validation to generate a predictive mode. Using a transformation function including a combination of no more than two relevant factors from the predictive model, the model can predict at least one structural characteristic of a newly tested object using the above and below described device with the transformation function without the need for said annotation and validation. In general, imaging using X-rays and transillumination may provide relatively noninvasive ways to diagnose the condition of an object, for example, of a patient's teeth. However, they are not a perfect substitute for actual extraction and detailed examination of an individual tooth. The challenge lies in how data captured from devices may be interpreted as corresponding to specific physical issues at specific locations. Transillumination has been considered the standard in locating cracks or fractures in, for example, teeth. The blockage of light may indicate a significant structural crack or fracture.

Even with X-ray imaging, one is trying to gather information about a 3-dimensional object—a tooth—using a series of monochromatic 2-dimensional images that are subject to visual artifacts such as shadows. Today, expertise and experience are needed to properly interpret this data. Using the percussion devices described above and exemplified below may provide an objective and quantitative measurement to diagnose the conditions of an object.

The above described systems and methods of the present invention may not only detect the same cracks and fractures just as accurately as transillumination, but they may also detect cracks and fractures not detectable with transillumination and are not dependent on direct visualization.

The actual test data may be generated from an above and below described percussion system and method to generate a percussion response. The system may include a device having an energy application tool capable of applying energy to an object to generate that percussive response to reveal some structural characteristics of the object without substantially affecting the existing structural characteristics of the object, as noted above. The energy application tool may be programmed to impact an object a certain number of times per minute at substantially the same speed for a certain time interval during testing. The system may be useful for determining both the loss coefficient and the normal fit error (NFE).

In general, the relevant factor information described above, NFE and LC, are used to evaluate the structural characteristics of the object tested. These results may be validated using other detection methods, for example, from X-ray radiographs, magnification, transillumination, dye penetrants, occluding tests and ultrasonography for relatively non-invasive detection, to disassembly or even extraction in terminal situations.

An example of one of the instruments is described in U.S. Pat. No. 6,120,466 ("the '466 patent"). The loss coefficient may be manifested as follows: energy of an elastic wave attenuates relatively quickly in materials with a relatively high loss coefficient, whereas the energy of an elastic wave attenuates relatively slowly in materials with a relatively low loss coefficient. Other examples of instruments and devices that may be utilized may include, for example and without limitation, those described in U.S. Pat. No. 9,869,606, U.S. patent publication No. 20190331573, and/or PCT publication WO2019133946, which are incorporated by reference in their entireties.

The damping capacity or loss coefficient of an object is an important parameter in a wide variety of applications, for example, dentistry, constriction, and others. For example, in the field of dentistry, when a healthy tooth is subjected to an impact force, for example, the mechanical energy associated with the impact is primarily dissipated by the periodontal ligament. Changes in the structure of the periodontal ligament that reduce its ability to dissipate the mechanical energy associated with an impact force, and thus reduce overall tooth stability, can be detected by measuring the loss coefficient of the tooth. Additionally, changes that weaken the actual structural integrity of the tooth or implant itself can be detected by an increase in the loss coefficient.

The same system described above may measure, for the time interval, a percussion response such as energy reflected from the object or the deceleration of the energy application tool as a result of the energy application, for example, by tapping or applying energy on the object, namely energy return. The response may be fed to a computer and the information is recorded or compiled for analysis by the system, which may include creating a percussive response profile, for example, an energy return curve (ERG) as a time-energy profile, frequency-energy profile, based on the energy reflected from the object during the time interval, and/or evaluating the percussive response profile, for example, a time energy profile, to determine the structural characteristics of the object, for example, vibration damping capacities; acoustic damping capacities; defects including inherent defects in, for example, the bone or the material that made up the object; cracks, micro-cracks, fractures, microfractures; loss of cement seal; cement failure; bond failure; microleakage; lesions; decay; structural integrity in general or structural stability in general.

Other systems and devices, as already described above or are to be described below, may also be used for testing.

Figure 5:
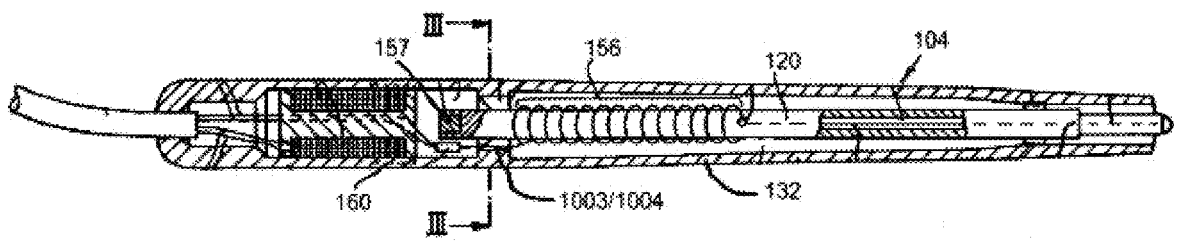
FIG. 5 illustrates a cross-sectional view of a handpiece showing the internals of the present invention.

FIG. 1 shows an embodiment of the device discussed above. In one embodiment, the system may include a handpiece 104, in the form of a percussion instrument. The handpiece 104 may have a cylindrical housing 132 with an open end 132a and a closed end 132b. The open end 132a is tapered as exemplified here, though other configurations are also contemplated. An energy application tool 120, for example, a tapping rod 120, may be mounted inside the housing 132 for axial movement, as noted above. The handpiece also includes a drive mechanism 160, mounted inside the housing 132 for driving the tapping rod 120 axially within the housing 132 between a retracted position 128 and an extended position 129 during operation. In the extended position 129, the free end of the tapping rod 120 extends or protrudes from the open end 132a of the housing 132, as shown. The drive mechanism 160 may include an electromagnetic coil 156, as shown in FIG. 5, to be discussed further below. The tapping rod 120 may have a permanent magnetic ensemble 157 mounted at the end away from the free end. The electromagnetic coil 156 of the drive mechanism 160 may be situated behind the other end of the tapping rod 120, resulting in a relatively small outside diameter for the handpiece 104.

Figure 6:
FIG. 6 illustrates a cross-sectional view of a tapping rod within the handpiece of FIG. 5.

The mounting mechanism for the energy application tool 120, for example, tapping rod 120 may be formed by bearings 1003 and 1004, as shown in FIG. 6, for receiving or supporting the tapping rod 120 in a largely friction-free manner. The magnetic or propulsion coil 156 may be situated in the housing 132 adjacent to the permanent magnet 157 and is axially behind the permanent magnet 157. The magnetic coil 156 and the permanent magnet 157 form a drive for the forward and return motion of the tapping rod 120. The drive coil 156 may be an integral component of the housing 130 and may be connected to a supply hose or line 1000.

The two bearings 1003 and 1004 may be substantially frictionless and may include, as shown in FIG. 6, a plurality of radially inwardly extending ridges separated by axial openings 1400. The axial openings 1400 of the bearing 1003 allow the movement of air between a chamber 1500 which is separated by the bearing 1003 from a chamber 1600, which chambers are formed between an inner wall surface of the housing 132 and the tapping rod 120. Air movement between these chambers 1500 and 1600 may thus compensate for movement of the tapping rod 120.

The housing may include an object contacting portion (not shown) or the object contacting portion may be part of the sleeve 108. Referring again to FIG. 1, a sleeve 108 is positioned towards the end 132a and extending beyond it. The sleeve 108 envelops the end of the housing 132a and is flattened at its end 116 for ease of positioning against a surface of an object 112 during operation. The sleeve aids in the positioning of the handpiece 104 on the object to stabilize the handpiece during operation. The sleeve 108 may also include a tab 110, as shown in FIG. 2a, protruding from a portion of its end 116, so that when the open end 116 of the sleeve 108 is in contact with a surface of the object 112 undergoing the measurement, the tab 110 may be resting on a portion of the top of the object 112, as shown in the FIG. 6. The tab 110 and the sleeve 108 both assist in the stabilizing and repeatable positioning of the handpiece 104 with respect to the object 112 and the tab 110 may be placed substantially at the same distance from the top of the object 112 every time. As noted above, the object may include an anatomical structure or a physical structure.

Figure 2:
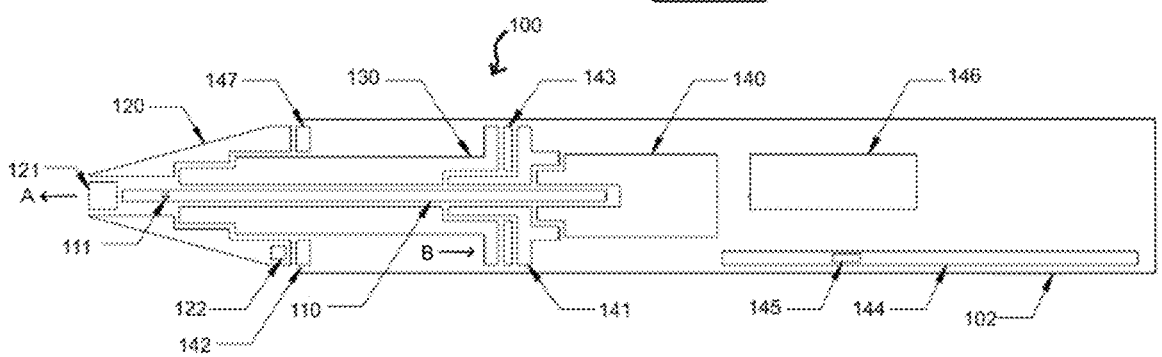
Figure 2A:
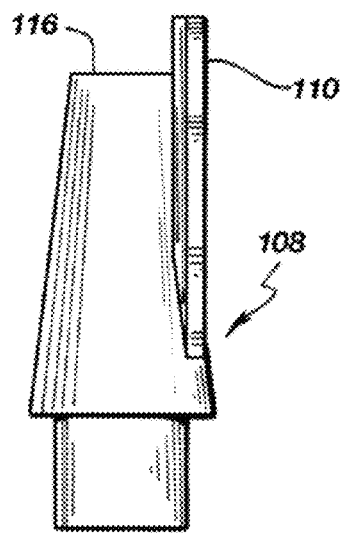
FIG. 2a illustrates an embodiment of a sleeve portion for the measurement devices of the present invention.

FIG. 2 depicts embodiments of other devices that are applicable for the present invention. The system may include a device that may be a desktop or a portable device. The system may include a handpiece 100 having a housing 102 which houses the energy application tool and sensing mechanism, as illustrated in the block diagram of FIG. 2. In general, a handpiece may refer to a handheld device, but may also include, without limitation, any other appropriate form for the desired application, such as mounted devices or tool/mechanically/robotically articulated devices, or any portable device. The handpiece 100 may also be referred to, for example, as a device or instrument interchangeably herein. In some embodiments, the energy application tool 110, as illustrated, may be mounted within the housing 102 for axial movement in the direction A toward an object, and such axial movement may be accomplished via a drive mechanism 140. Drive mechanism 140 may generally be a linear motor or actuator, such as an electromagnetic mechanism which may affect the axial position of the energy application tool 110, such as by producing a magnetic field which interacts with at least a portion of the energy application tool 110 to control its position, velocity and/or acceleration through magnetic interaction. For example, an electromagnetic coil disposed at least partially about the energy application 110 may be energized to propel the energy application tool 110 forward toward the object to be measured, as illustrated with the electromagnetic coil 140. The electromagnetic coil may also, for example, be alternatively energized to propel the energy application tool 110 backward to prepare for a subsequent impact. Other elements, such as rebound magnetic elements, may also be included, such as to aid in repositioning of the energy application tool 110 after propelling via the electromagnetic coil. The drive mechanism 140 and/or other portions of the instrument may generally be powered by a power source, as shown with power source 146, which may be a battery, capacitor, solar cell, transducer, connection to an external power source and/or any appropriate combination. An external connection to a power source, either to power the handpiece 100 or to charge the internal power source, such as the power source 146, may be provided, such as a power interface 147 in FIG. 2, which may include, for example, a power contact for direct conductive charging, or the power interface 147 may utilize wireless charging, such as inductive charging.

Figure 3:
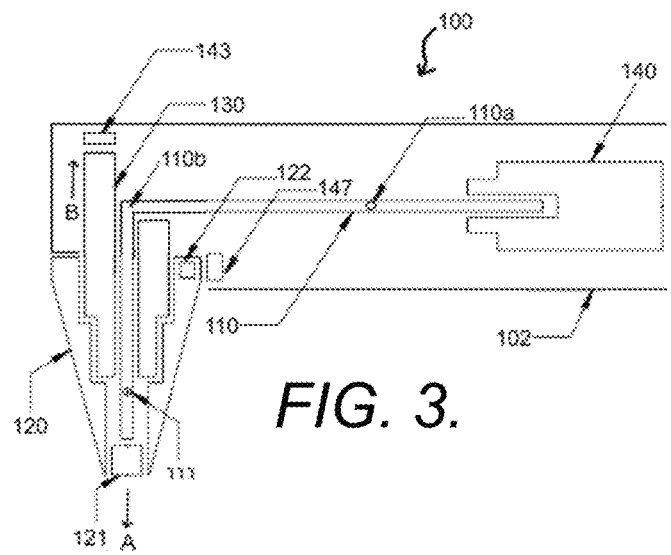

In some other embodiments, the energy application tool 110 may be utilized to move substantially in a direction A which may be perpendicular or substantially perpendicular to the longitudinal axis of the housing 102, as illustrated in the block diagram of a handpiece 100 in FIG. 3. As illustrated, the energy application tool 110 may, for example, be substantially L-shaped to accommodate the interaction with the drive mechanism 140 and protrude in direction A, substantially perpendicular to the axis of the housing 102. As illustrated in an example, the drive mechanism 140 may act on the energy application tool 110 to cause it to rock on a pivot 110a, causing it to move in direction A at its tip. The drive mechanism 140 may utilize, for example, an alternating magnetic element which may act on the energy application tool 110 to cause it to move alternatingly in two directions, such as up and down. In another example, the bend portion of the L-shaped energy application tool 110, such as shown with bend 110b, may include a flexing and/or deformable construction such that a linear force applied by the drive mechanism 140 may push the energy application tool 110 in the direction A at the tip by conveying the forward motion around bend 110b. For example, the bend 110b may include a braided, segmented, spring-like and/or otherwise bendable section that may also convey motion and/or force around a bend. In general, the shape of the L-shaped energy application tool 110 may generally include other angles besides 90 degrees, such as between approximately +/−45 degrees from the rearward portion 110d. In some embodiments, the energy application tool 110 may also include multiple portions which may be separable, such as portions 110c and 110d, such that, for example, the portion 110c may be removed and disposed between uses or patients, such as to aid in preventing cross-contamination. In general, the separable portions may include an interface to couple them for use in a measurement such that they substantially act as a unitary energy application tool 110, as described below.

Figure 4:
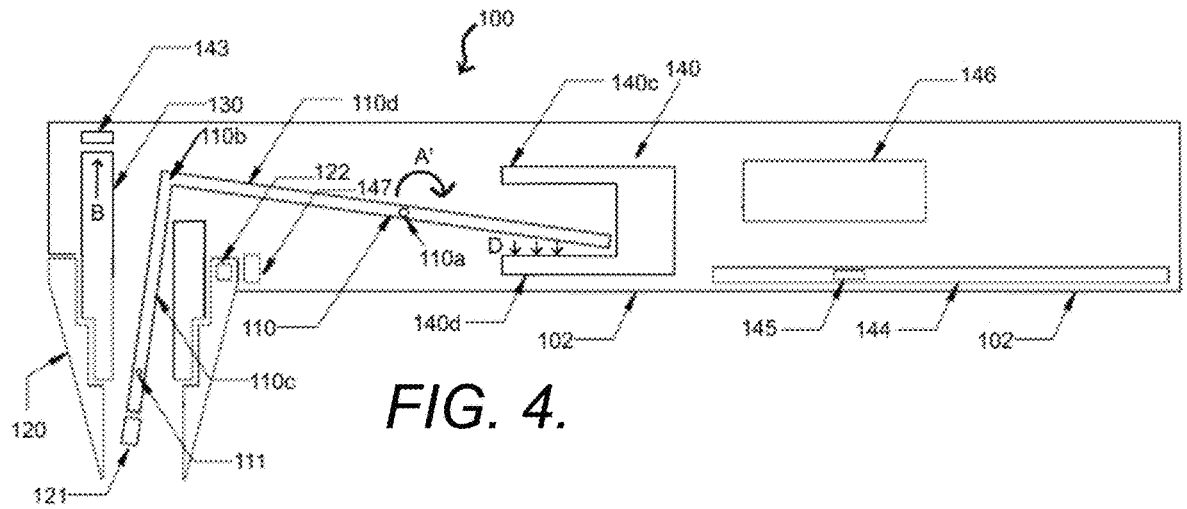
Figure 4A:
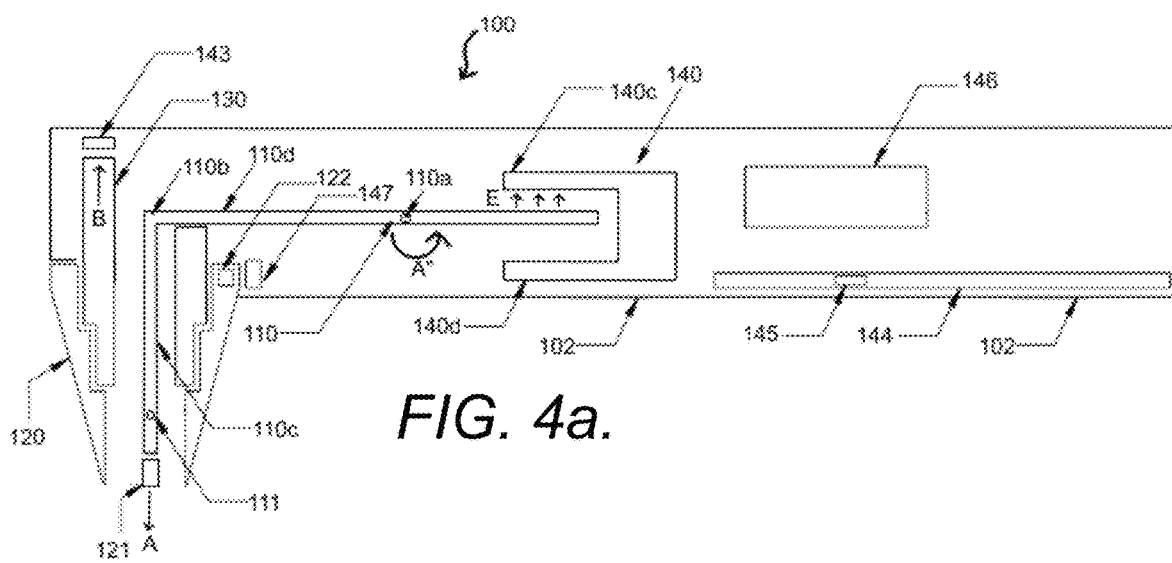

In some embodiments, the L-shaped energy application tool 110 may rock on a pivot 110a, such as, for example, with an external force applied from a drive mechanism 140, as shown in FIGS. 4 and 4a. For example, the drive mechanism 140 may apply alternating forces to the energy application tool 110 to cause it to rock about the pivot 110a, such as with a force applied D from portion 140d applied to the rearward portion 110d to cause rocking in direction A' away from a target object, as shown in FIG. 4, or with a force applied E from portion 140c applied to the rearward portion 110d to cause rocking in a direction A" toward the target object such that the energy application tool 110 is driven in direction A, as shown in FIG. 4a. The forces D and E may be applied by any appropriate method, such as, for example, by applying a magnetic force on the energy application tool 110, which may contain a magnetic or metallic element which may respond to the application of force from the drive mechanism 140. In general, the shape and arc of the rocking motions A' and A" may be designed such that the energy application tool 110 impacts the target object in a direction substantially perpendicular to the target object surface, as shown with the rocking A" into a substantially vertical orientation of the bent portion 110c around bend 110b in FIG. 4a. To reset the device 100 for a subsequent measurement, the portion 140d may apply a return force D, as shown in FIG. 4, to cause rocking A' to return the energy application tool 110 to a withdrawn or resting state. In general, the interior of the device 100 may be adapted to allow for the rocking motions A' and A" without interfering with the energy application tool 110.

Any of the devices described above, for example, a handpiece 100, delivers a free-floating energy application tool, such as the energy application tool 110 or 120, for example, a tapping probe to the object, for example a tooth and/or implant with a consistent kinetic energy just prior to each percussion of the object. From the resulting data, the energy returned to the energy application tool be normalized by the kinetic energy of the energy application tool prior to impact vs time may be determined and analyzed. The response, such as a percussion response is plotted as Percent Energy Return (ER) on the vertical axis and Time (micro seconds or μs) on the horizontal axis. Each ER value is measured and plotted, at time increments of, for example, 4 μs along the horizontal axis. The vertical axis can autoscale to the highest ER value and the horizontal axis may range from 0 to 0.5 ms (milliseconds), as shown in the percussion response curves of FIGS. 7 and 8. The numerous ERGs of FIGS. 7 and 8 may be representative of tests on numerous defect free objects or numerous objects with defects, respectively.

In exemplary embodiments, a sensor may be disposed in a manner to measure the force exerted by the operator on the object via contact with the handpiece 100. For example, the sensor may thus be positioned, for example, between the object and the handpiece. The sensor may also be placed to receive transduced or transmitted force from the portion of the handpiece in contact with the object. The sensor may further be positioned between the handpiece and the operator in a manner that allows it capture the force applied. In some embodiments, an internal force sensor may be utilized which may rely on transduction or transmission of the normal force from contact with the object through portions of the handpiece 100.

Figure 1A:
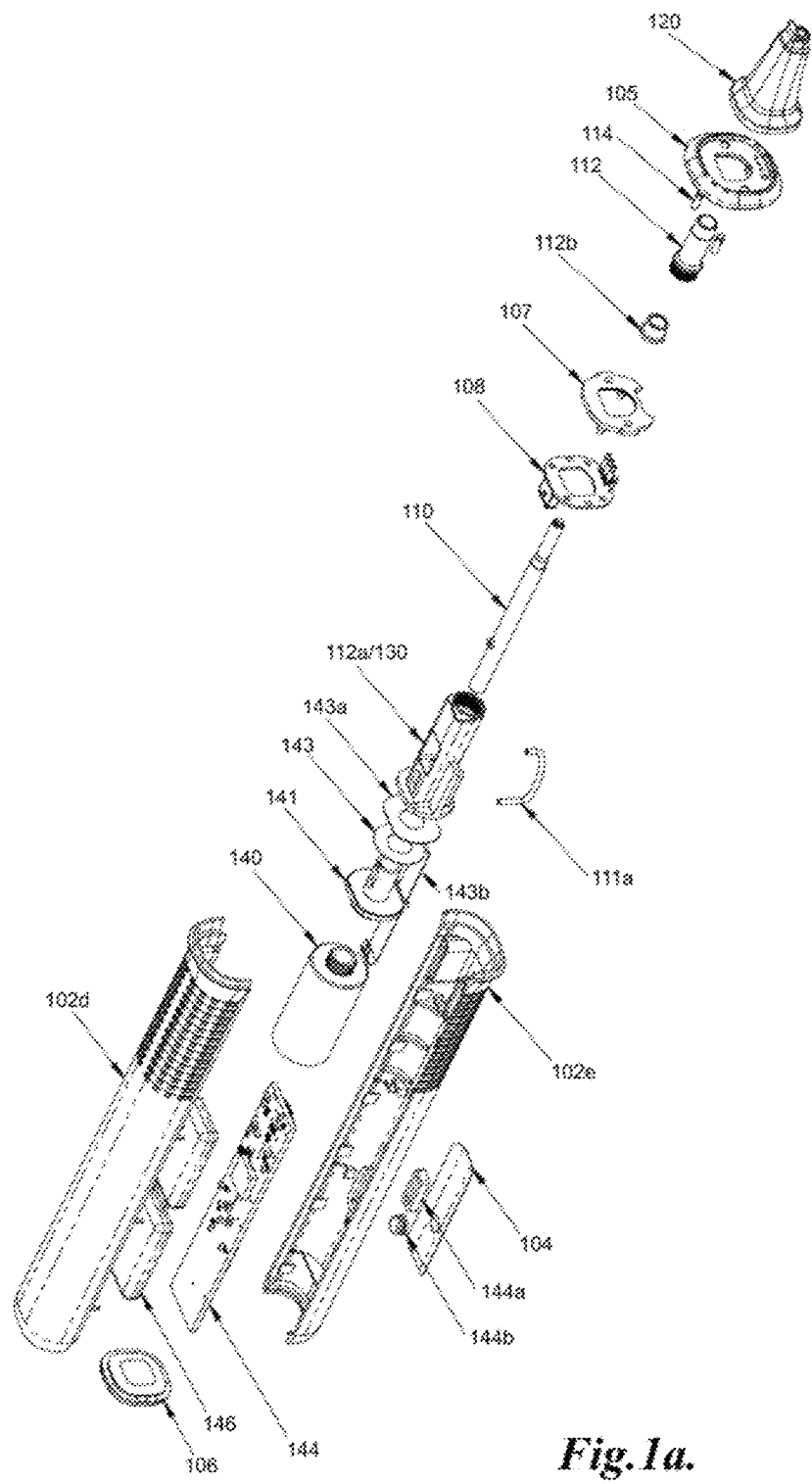
FIG. 1a illustrates an exploded view of a handpiece with a sleeve portion.

FIG. 1a illustrates an arrangement where the contact of a portion of the handpiece 100, such as the sleeve portion 120, may push on a force transfer member 130, such as a force transfer sleeve or sleeve-like component, which may then exert a force by pushing in direction B on a force sensor 143. A force sensor 143 may include any appropriate sensor for measuring the force being exerted from the contact of the handpiece 100 against an object by the user, such as, for example, a piezoelectric sensor, a force sensing resistor (e.g. a Shunt-mode FSR), a strain gauge or multiple strain gauges (e.g. mounted onto a cantilever(s) that flex in response to the applied force), linear position sensors (e.g. optical position sensors, magnetic field or other than can detect a position change of a component pressing against a spring or other element where the linear position change corresponds to the applied force), and/or any other appropriate type of force sensors. The force sensor 143 may further take on any appropriate shape or form, such as, for example, a flattened sensing pad, which may be in a ring shape that surrounds the energy application tool 110 as illustrated (such as to maintain separation of the energy application tool 110 from the contact forces being measured by the force sensor 143), or shapes such as ellipsoids, polygons or other shapes that may be positioned in the handpiece 100 to detect the contact force. In the exploded views of FIG. 1a, the force sensor 143, for example, is sandwiched between a relative fixed component. As illustrated in FIG. 1a, the force sensor 143 may be sandwiched between the drive mechanism interface member 141, which itself is rigidly mounted to the drive mechanism 140 as discussed further below, and components that transfer force to the force sensor 143, as shown with the stacking of sleeve 120 (if present), transfer sleeve 112 and the sleeve mount 112a/force transfer member 130, which may pass through the apertures of the portions of the housing, as shown with forward end cap 105 and/or the sleeve mount PCB 108 and its retainer 107. The force sensor 143 may be, for example, held in a relative fixed position by mounting onto a rigid portion of the handpiece 100, such as the drive mechanism interface member 141, which may, for example, be coupled to drive mechanism 140 and/or to the housing 102 of the handpiece 100 such that it is in a relative fixed position with regard to the operator. The force sensor 143 may then detect the load originating from the contact with object 90 as biased against the relative fixed portion, such as the drive mechanism interface member 141. It may generally be understood that intervening components or portions between the object contact and the force sensor 143 may be present or not present so long as a full transduction/transmission path for the force remains for operation.

The force sensor 143 may alternatively be sandwiched between the drive mechanism 140 and a mounting bracket 148, which itself is rigidly mounted to the body of the handpiece 100, and components that transfer force to the force sensor 143, as shown with the stacking of sleeve 120

(if present), transfer sleeve 112, the sleeve mount 112a/force transfer member 130 (which itself is rigidly mounted to the drive mechanism 140) which may pass through the apertures of the portions of the housing, as shown with forward end cap 105 and/or the sleeve mount PCB 108 and its retainer 107. A force sensor 143 may include any appropriate sensor for measuring the force being exerted from the contact of the handpiece 100 against an object by the user, such as, for example, a piezoelectric sensor, a force sensing resistor (e.g. a Shunt-mode FSR), a strain gauge or multiple strain gauges (e.g. mounted onto a cantilever(s) that flex in response to the applied force), linear position sensors (e.g. optical position sensors, magnetic field or other than can detect a position change of a component pressing against a spring or other element where the linear position change corresponds to the applied force), and/or any other appropriate type of force sensors. The force sensor 143 may further take on any appropriate shape or form, such as, for example, a flattened sensing pad, which may be in a ring shape that surrounds the energy application tool 110 as illustrated (such as to maintain separation of the energy application tool 110 from the contact forces being measured by the force sensor 143), or shapes such as ellipsoids, polygons or other shapes that may be positioned in the handpiece 100 to detect the contact force. The force is then transferred through the drive mechanism 140 to the force sensor 143 as biased against the mounting bracket 148. This arrangement may be desirable, for example, to decrease flexing or misalignment of components, such as the drive mechanism 140 and the energy application tool 110 as they are rigidly connected to each other with a flexing fulcrum being generally present outside of these components1a1a. Such potential flexing or misalignment may be undesirable, for example and without being bound to any particular theory, in uses of the handpiece 100 other than at a normal angle to the surface of an object. The increased rigidity in connections between the drive mechanism 140 and the energy application tool 110 may aid in reducing any variation in transfer of energy from the drive mechanism 140 and the energy application tool 110 when the handpiece is subjected to flexing or uneven loading when pressed against an object 90, such as when pressing the handpiece 100 against an object 90 at an angle, for example.

In some embodiments, a force transducing or transmitting member may be utilized without the sleeve 120, which may be used to contact the object.

In embodiments of the system using a sleeve portion, a sleeve portion 120 may be mounted onto the force transfer member 130, such as onto sleeve mount 112a which may be coupled to or form a portion of force transfer member 130 and may extend out of the housing 102 via aperture 102a. The force from contact with the object may then be transferred. The normal force from holding the sleeve portion 120 against the object may cause the sleeve 120 to push against the transfer sleeve 112, which may be a portion of or couple to the force transfer member 130, which may then exert the force in direction B on the force sensor 143, which may be biased against a rigid and/or relative fixed portion of the handpiece 100, such as the drive mechanism interface member 141, which may be mounted to the drive mechanism 140, which itself may be mounted to the housing 102, such as via drive mountings 140a, or sandwiched between the drive mechanism 140 and the mounting bracket 148 which may be mounted to the housing 102, such as via drive mountings 140a.

In some embodiments, portions of the handpiece 100 may be movable relative to the rigid and/or relative fixed portion (s). This may be desirable to aid in transferring of force from the contact with the object to the force sensor and for providing a physically perceivable feedback to the operator of the exertion of contact force.

In some embodiments, multiple components may be utilized to form the force transfer member 130, such as for ease of manufacturing, assembly, replicability of parts, etc. For example, as illustrated, the force transfer member 130 may include separate parts transfer sleeve 112, sleeve mount 112a and force transfer base portion 130b, which may attach or at least contact to provide force transfer, such as at transfer member contacts 130a.

The force transfer member 130 and its mechanically coupled portions, such as the sleeve portion 120, transfer sleeve 112, sleeve mount 112a and force transfer base portion 130b, may be movable, such as in direction B, relative to the relative fixed portions, such as the force sensor 143, drive mechanism interface member 141, drive mechanism 140 and housing 102. A biasing member, such as the force sensor bias 143a, may further be provided between the force transfer member 130 and the force sensor 143, such as to, for example, distribute the force on the force sensor 143 evenly and/or to serve as a return bias to return the force transfer member 130 to its original position along direction B when the contact with the object ceases, such as via a bias or leaf spring, or elastic cushion. In general, the movement of the components that transfer force to the force sensor 143, such as the sliding distance caused by the contact force, may be very small, for example, in the order of about 0.3 mm to about 1 mm, more for example about 0.5 mm.

The force transfer member 130 and its mechanically coupled portions, transfer sleeve 112, sleeve mount 112a and drive mechanism 140, may be movable, such as in direction B, relative to the relative fixed portions, such as the force sensor 143, mounting bracket 148 and housing 102. A biasing member, such as the force sensor bias 143a, may further be provided between the drive mechanism 140 and the force sensor 143, such as to, for example, distribute the force on the force sensor 143 evenly and/or to serve as a return bias to return the drive mechanism 140 to its original position along direction B when the contact with the object ceases, such as via a bias or leaf spring, or elastic cushion. In general, the movement of the components that transfer force to the force sensor 143, such as the sliding distance caused by the contact force, may be very small, for example, in the order of about 0.3 mm to about 1 mm, more for example about 0.5 mm.

In embodiments with an electrical contact between the sleeve portion 120 and the handpiece 100, such as the security feature 122 interacting with electronic contacts 113, movement between the sleeve 120 and the handpiece 100 may be compensated for, such as with spring pins and or placing electrical contacts such that contact is maintained through any motion of the sleeve 120 while mounted on the handpiece 100, such as by placement on parallel surfaces or on the movable portions, such as the sleeve mount 112a.

The sleeve portion 120 may also be mounted onto a force transfer member 130 that forms a permanent part on the front of the housing 102, and shields the energy application tool 110, for example, a tapping rod, from damage when no sleeve portion is present, for example, the sleeve portion forms part of a disposable assembly, as discussed above and/or below.

In some embodiments, as discussed above, the sleeve 120 and/or the energy application tool 110 may be disposed substantially perpendicular to the housing 102. The holding force against the object may then act in direction, and as such the sleeve 120 may press in a direction against a force transfer member 130 onto a force sensor 143, which may be mounted and/or positioned against a relative fixed point, such as against the housing 102 as illustrated.

The energy application tool 110, for example, a tapping rod, may be enabled or triggered when the object contacting portion of the sleeve portion, such as the contact portion 121 of the sleeve 120, is pushed against an object undergoing measurement, for example, a tooth and a force within a certain range may be detected. When the correct force is detected, the handpiece 100 is turned on or enabled to start the measurement.

For example, with dental procedures on human teeth, an appropriate contact force may be about 3 N to about 10 N for example, more for example about 5 N to about 8 N of force. In general, the force sensor 143 may read the actual contact force or may read a transferred, transduced or transmitted force which differs from the actual contact force, which may be interpreted or correlated to the actual contact force by the handpiece 100, such as with electronics assembly 144. The measurement of the contact force may further be corrected, such as due to orientation of the handpiece 100 in the gravitational field, with input from an accelerometer or other appropriate device to detect orientation, as illustrated in FIG. 2 with orientation sensor 145.

The sensor, for example the force sensor 143, may be in physical proximity and/or contact and/or coupled with at least a portion of the handpiece 100 other than the energy application tool 110, for example, it may be in physical proximity and/or contact and/or coupled with the sleeve portion 120, if the open end of the sleeve portion 120 may include an object contacting portion 123, as noted above. In some embodiments of the invention, the sensor may include at least one strain gauge for sensing. The strain gauges may be attached or mounted to a cantilever between the device housing and the sleeve portion so that when the object contacting portion of the sleeve portion is pressed on the object it also deforms the cantilever which is measured by the strain gauge, thus providing a force measurement. In some embodiments, multiple strain gauges mounted to a single or to separate cantilevers may be utilized. The cantilever(s) may also, for example, be present on a separate component from the rest of the housing or sleeve portion, such as, for example, on a mounting device. According to one aspect, the force sensing may be done by a linear position sensor, which would know, for example, that if the force transfer sleeve like portion is at position X, a force of Y has to be applied to it (against the reaction force of the spring) to move it to that position. According to another aspect, the force sensing may be performed by an optical sensor, for optically sensing the position of the moving part, when it is pushed against a spring, In some embodiments of the invention, the relative position of the object contacting portion of the sleeve portion on the object may be determined by having one or more strain gauges which may be attached at one end to a moving part, for example, a force sensor sleeve like component, and the other end to a static element, for example, the housing. In some embodiments of the invention, the device may include piezoelectric elements for directly measuring the force. In some embodiments of the invention, a hall effect sensor may be used to detect a change in the magnetic field when a magnet (attached to the moving element) is moving relative to the position of the sensor. In some embodiments of the invention, a capacitive linear encoder system, like that found in digital calipers may be used to measure the force.

The sensing pad may include a layer structure, which may be generally referred to as a "Shunt Mode" FSR (force sensing resistor) that may change resistance depending on the force applied to the pad, to provide a force measurement. FSRs typically consist of a conductive polymer, which changes resistance in a predictable manner following application of force to its surface. The sensing film of the FSR typically includes both electrically conducting and non-conducting particles suspended in a matrix. Applying a force to the surface of the FSR causes particles to touch the conducting electrodes, changing the resistance of the FSR. FSRs may be desirable for their low size, such as with a thickness typically less than 0.5 mm, low cost and good shock resistance.

Piezoelectric sensors may also be utilized that convert pressure exerted on the force sensor 143 into a change in electrical characteristics, such as a voltage across the piezoelectric element.

A strain gauge or other similar element may also be included on a leaf spring or other biasing member, such as the force sensor bias 143a.

In some exemplary embodiments, the force sensor may be in electronic communication with the energy application tool 110 and may act as an on/off switch or activation switch for the handpiece 100. For example, when a proper force is exerted on the object by the object contacting portion of the sleeve, it may trigger the activation mechanism of the instrument to activate the movement of the energy application tool 110 to start a measurement. Thus, no external switches or push buttons are needed to activate the on and off of the system, as noted above. The indication of the proper force may be indicated by visible or audible signals.

In some embodiments, the contact of the handpiece 100 with the object, such as with the sleeve portion 120 may transfer contact force, such as the normal force from the contact, to the force sensor 143. The force sensor 143 may measure the contact force or a transferred force and produce a signal or change in characteristic, such as resistance, voltage, etc. The signal or change in characteristic may then be relayed to the control mechanism, such as in the electronics assembly 144. The control mechanism may then determine if the contact force is in an acceptable range, for example 5-8 N. If the force is in the range, the control mechanism may enable the energy application tool 110 to operate and/or output a signal to the user that the contact force is acceptable. If the contact force is out of the acceptable range, the control mechanism may output a signal to the user to change the pressure and/or disable or keep disabled the energy application tool 110. If acceptable, the control mechanism may also initiate the energy application tool 110 automatically and perform a measurement. Afterwards, the control mechanism may be reset for a new measurement.

In some embodiments, the energy application tool 110 may be instantaneously turned on once a proper contact force is exerted by the contact portion 121 (or other portion of the sleeve 120 or handpiece 100, as appropriate) on the object, as indicated by visible or audible signals. FIG. 1a illustrates operator signals, as shown with light sources 114, which may provide signals to the operator about the contact force. In some embodiments, there may be a delay prior to activating the energy application tool 110 once a proper contact force is exerted on the object, as indicated by visible or audible signals, as above. In a further embodiment, once a certain push force on the object is detected and maintained for a period of time, for example, about 0.5 seconds, the instrument may be turned on to start measurement.

In some embodiments, the force measurement may be connected to a visual output, such as lights. Lights may be mounted at any convenient location on the instrument, for example, one or multiple LEDs may be mounted at the front of the instrument, as shown with light sources 114. For example, a multiple light system may be included. For example, two LEDs may be used, such as green for acceptable and red for unacceptable contact force.

In some embodiments, a light from the light sources 114 lights up the sleeve 120, which may be transparent or translucent, to indicate acceptable or unacceptable contact force.

The proper force exerted by the operator on the object acts as a switch of the system. When the system is not switched on, it may be desirable to know whether it has malfunction, not sufficient force or too much force is exerted. In some embodiments, if the user is pushing too hard on the object, the light may change first to amber, then to red, such as indicated via output from the light sources 114. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another example, no light may indicate too little force, a green light may indicate the right amount of force, while a red light may indicate too much force. In yet another example, a one light system may be included. For example, no light may give a signal of too little force and a red light may give a signal of too much force. In a further example, a flashing red light may indicate too much force and no light may indicate too little force. The LEDs may be mounted on the surface of the handpiece 100, or they may be internal to the housing 102 and light may be conveyed via light pipes or fiber optic channels, which may present at the surface of the housing 102, such as at the light sources 114 shown as light pipes in FIG. 1*a*. In some examples, the light pipes 114 may be integral or attached to a portion of the handpiece 100, such as retainer 107 in FIG. 1*a*.

In some embodiments, the light pipes 114 may extend into the sleeve portion 120 such as to better carry light toward the object and/or to better illuminate the sleeve portion 120 for a user's perception. Light emanating from the light pipes 114 may then illuminate the sleeve portion 120, which may, for example, be adapted to diffuse the light toward the object and/or in a manner to be easily observable by the user, such as by inclusion of light diffusing material(s), additive(s) and/or by physical treatment, such as frosting and/or any other appropriate treatment. The light pipes 114 may also be utilized to provide additional alignment, connection and/or securement between the sleeve portion 120 and the handpiece 100, such as by fitting into the slots 125*a* of the sleeve portion 120. For example, the utilization of one or more light pipes 114 fitting into slots 125*a* may aid in providing resistance to rotation about the longitudinal axis by the fitting between the light pipes 114 and the slots 125*a* (e.g. by close or friction fitting).

In another embodiment, the force measurement may be connected to an audible output. In one example, the audible output may include a beeping sound to indicate too little force and a multiple beep to indicate too much force. In another example, the audible output may include a beeping sound to indicate too little force and a beeping sound with a flashing red light to indicate too much force, such as via the light sources 114 or as discussed above with internal light sources. In a further example, the force measurement may be connected to a voice alert system for alerting too much force or too little force. In yet a further example, the force measurement may be connected to a voice alert system to alert too little force and a voice alert and a flashing red light for alerting too much force.

The handpiece 100 may also include a reset button, such as shown with reset control 144*b* in FIG. 1*a*, such as to reset the handpiece 100 to re-attempt placement with a proper force after an initial incorrect placement. The reset button 144*b* may press onto an appropriate control on the electronics assembly 144 to place the handpiece 100 in a renewed state.

Other examples of devices may include, for example and without limitation, those described in U.S. Pat. Nos. 6,120,466, 9,869,606, U.S. patent publication No. 20190331573, and/or PCT publication WO2019133946, which are incorporated by reference in their entireties.

When the force sensor acts as an on/off switch, it may also act to monitor that a proper force is exerted on the object during measurement and/or a proper alignment of the handpiece 100 against the object during measurement is obtained. An inclinometer as shown with orientation sensor 145, may be present, for example, as part of an electronic control system, which may trigger an audible warning when the device is outside of the angular range of operation, for example, for a tapping rod, it may trigger the warning when it is plus/minus 30 degrees from horizontal. If the device is oriented such that the axis of operation is greater than 30 degrees from horizontal when a push force is sensed on the object contacting portion of the sleeve portion, it may result in a warning sound being emitted by a speaker located on the device, such as the PCB within the device. In such circumstances, the percussion action will not begin until the device is returned to an acceptable angle. In some instances, if the percussion action has started when the above mentioned departure from the range is detected, the device may not actually stop operation, but may simply be sounding an alarm, so that corrections may be made.

Common implementations of tilt sensors and inclinometers may include, but are not limited to, accelerometer, liquid capacitive, electrolytic, gas bubble in liquid, and pendulum-type systems. Traditional spirit levels and pendulum-based electronic leveling instruments are usually constrained by only single-axis and narrow tilt measurement range. However, most precision leveling, angle measurement, alignment and surface flatness profiling tasks essentially involve a two-dimensional surface plane angle rather than two independent orthogonal single-axis objects. Two-axis and three-axis inclinometers are typically built with micro electro-mechanical systems (MEMs) tilt sensors provides simultaneous two-dimensional angle readings of a surface plane tangent to earth datum.

MEMS tilt sensors typically employ accelerometers for functionality. Conceptually, an accelerometer behaves as a damped mass on a spring, where the accelerometer experiences an acceleration and the mass is displaced to the point that the spring is able to accelerate the mass at the same rate as the casing. The displacement is then measured to give the acceleration. In commercial devices, piezoelectric, piezoresistive and/or capacitive components are commonly used to convert the mechanical motion into an electrical signal. Piezoelectric accelerometers rely on piezoceramics (e.g. lead zirconate titanate) or single crystals (e.g. quartz, tourmaline). They typically offer favorable characteristics in application, such as upper frequency range, low packaged weight and high temperature range. Piezoresistive accelerometers are typically preferred in high shock applications. Capacitive accelerometers typically use a silicon micromachined sensing element, where their performance is superior in the low frequency range and they can be operated in servo mode to achieve high stability and linearity. Modern accelerometers are often small MEMs comprising a cantilever beam with a proof mass. Damping results from the residual gas sealed in the device. Under the influence of external accelerations the proof mass deflects from its neutral position. This deflection is measured in an analog or digital manner.

In an example of the use of an orientation sensor 145 in the form of a three-axis accelerometer mounted to the electronics assembly 144, the handpiece 100 was held against an object at angles between 30 degrees of incline and decline and the values returned from the accelerometer were utilized to create variations in the activation of the drive mechanism 140.

The following table shows the values returned from the accelerometer in the three axes at the following inclines/declines:

TABLE 1

| Angle | X | Y | Z |
|---|---|---|---|
| 30 degrees decline | −11 | 36 | −46 |
| 25 degrees decline | −10 | 31 | −49 |
| 20 degrees decline | −9 | 27 | −51 |
| 15 degrees decline | −8 | 21 | −53 |
| 10 degrees decline | −7 | 15 | −54 |
| 5 degrees decline | −7 | 9 | −55 |
| Horizontal | −7 | 0 | −55 |
| 5 degrees incline | −4 | −4 | −55 |
| 10 degrees incline | −3 | −10 | −54 |
| 15 degrees incline | −2 | −15 | −53 |
| 20 degrees incline | −1 | −21 | −52 |
| 25 degrees incline | 1 | −26 | −50 |
| 30 degrees incline | 2 | −32 | −47 |

The values were utilized to create a preprogramed set of instructions to vary the activation of the drive mechanism 140 when utilizing the energy application tool 110 at different inclinations to aid in evening out the force applied to approximately 25 N. In an example, the drive mechanism 140 was engaged for 22 milliseconds with a delay of 11 milliseconds before retracting (fixed timing) and yielded the measured applied force from the energy application tool 110 at different inclinations in the following table. Utilizing the preprogrammed set of instructions for different inclinations, the engaging time and delay time of the drive mechanism 140 was varied and yielded the following measured applied force from the energy application tool 110.

TABLE 2

| | Fixed Timing 22/11 (ms) | | Variable Timing | |
|---|---|---|---|---|
| | Average Force (N) | Target Force (N) | Average Force (N) | Drive/Delay (ms) |
| 30 degrees decline | 36.9 | 25 | 23.2 | 16/10 |
| 25 degrees decline | 35.6 | 25 | 25.5 | 17/11 |
| 20 degrees decline | 35.1 | 25 | 23.5 | 17/11 |
| 15 degrees decline | 33.7 | 25 | 25.6 | 18/11 |
| 10 degrees decline | 32.2 | 25 | 26.7 | 19/11 |
| 5 degrees decline | 30.0 | 25 | 24.4 | 19/11 |
| Horizontal | 27.5 | 25 | 26.3 | 21/11 |
| 5 degrees incline | 25.2 | 25 | 23.9 | 21/11 |
| 10 degrees incline | 23.1 | 25 | 24.2 | 22/11 |
| 15 degrees incline | 21.4 | 25 | 24.5 | 23/11 |
| 20 degrees incline | 18.7 | 25 | 24.7 | 24/12 |
| 25 degrees incline | 16.1 | 25 | 25.5 | 25/12 |
| 30 degrees incline | 12.3 | 25 | 26.1 | 27/13 |

The measured forces show that the preprogrammed set of instructions yielded much closer force values to the target force of 25 N than with the fixed timing in the first column. The varying of the activation of the drive mechanism 140 based on the inclination determined by the orientation sensor 145 may thus be utilized to produce a more consistent applied force from the energy application tool 110 based on the measured angle of inclination.

The device and/or a portion of the housing may also have an antimicrobial coating coated thereon capable of eliminating, preventing, retarding or minimizing the growth of microbes, thus minimizing the use of high temperature autoclaving process or harsh chemicals and may increase the kind and number of materials useful as substrates for making such tools or instruments.

Figure 7:
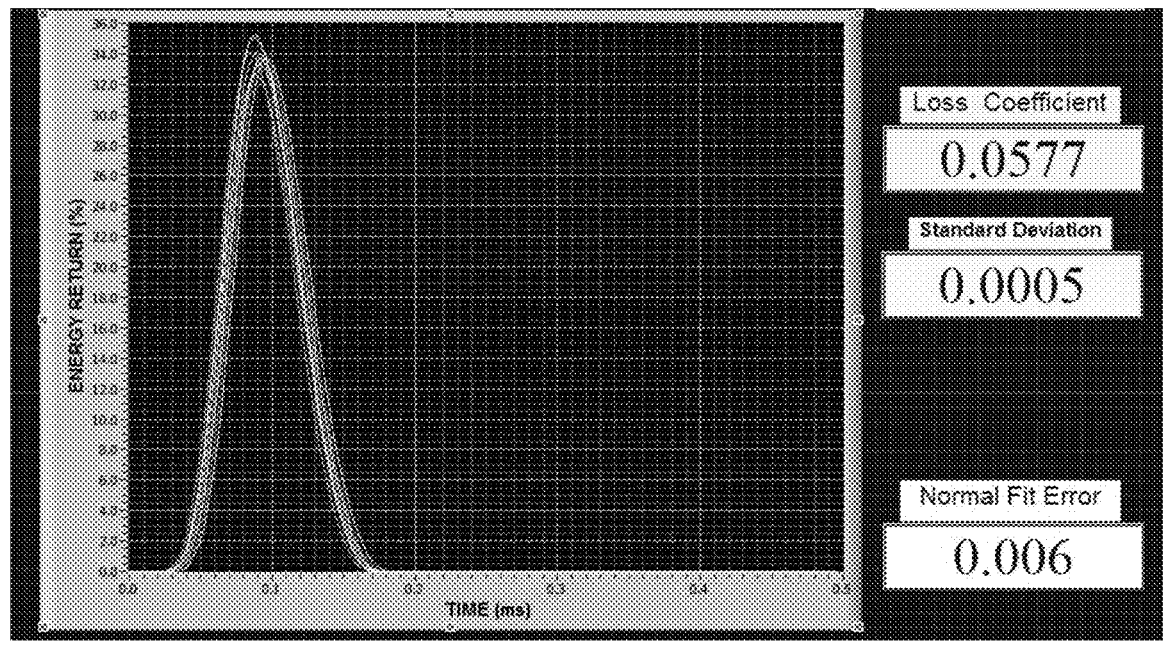
FIG. 7 illustrates an energy return curve and associated data from an undamaged tooth using the device and software of the present invention.
Figure 8:
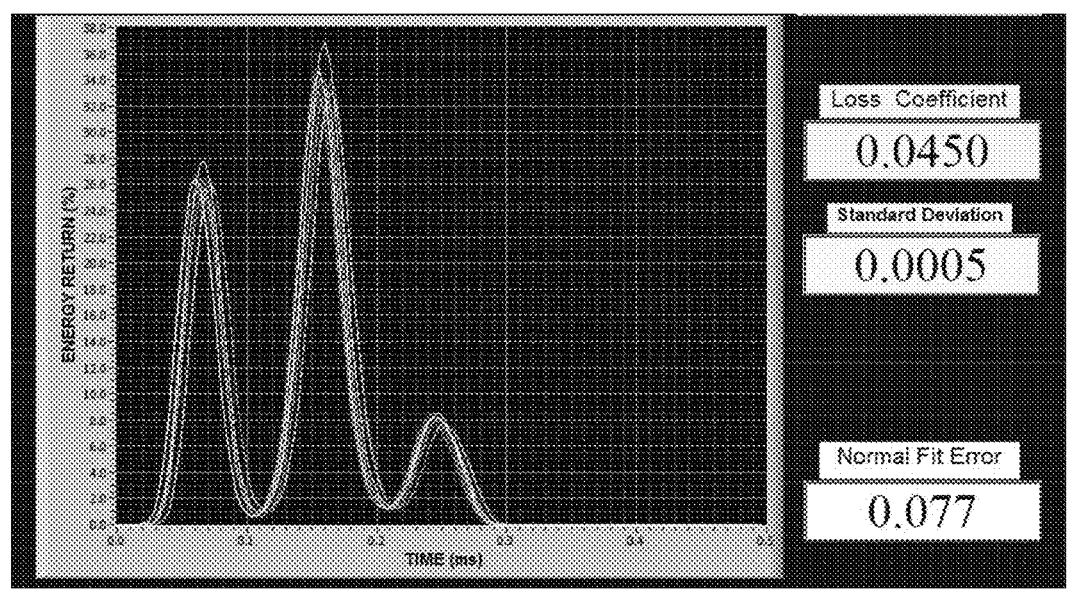
FIG. 8 illustrates an energy return curve and associated data from a damaged tooth using the device and software of the present invention.

The same percussion response as shown in FIG. 7 or 8, from a tooth or an implant may be analyzed by two different methods. The first method analyzes the percussion response for the tooth/implant mobility using Loss Coefficient (LC) characteristics whereas the second method analyzes the same percussion response for the tooth/implant internal/proximal mobility using Normal Fit Error (NFE) characteristics. The results of the percussion response for a dental setting, including ER graph, LC and NFE values are displayed on the computer screen for the clinician's review. Thus each one of the curves in FIGS. 7 and 8 illustrate typical representations of computer screen displays of percussion responses for a tooth with no pathology and with structural pathology, respectively.

The device may be coupled to a computer that uses an additional path to analyze the percussion response to generate mobility of the object and its associated fixed structures for example, teeth and/or implants. The software assesses the characteristics of the teeth and implants by identifying the presence of any structural characteristics or pathology (e.g. crack) within the internal and/or proximal structure of tooth or implant. As the tooth structure breaks down over time due to the normal tooth/implant wear and parafunction, the level of structural pathology may increase over time resulting in development of additional mobility.

Figure 11:
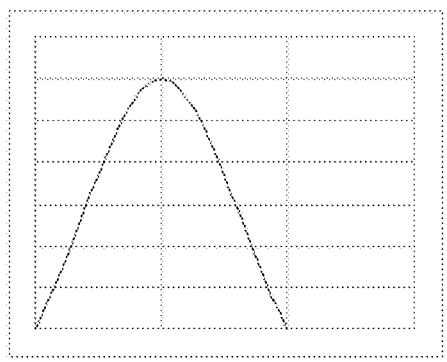
FIGS. 11, 11a, 11b and 11c illustrate general Energy Return Graphs (ERGs) from teeth having different levels of pathology.
Figure 11A:
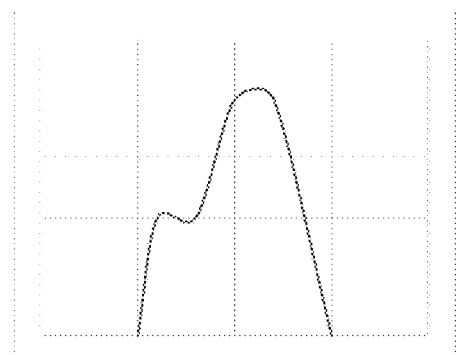
Figure 11B:
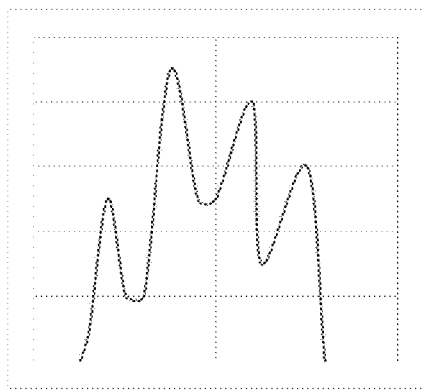
Figure 11C:
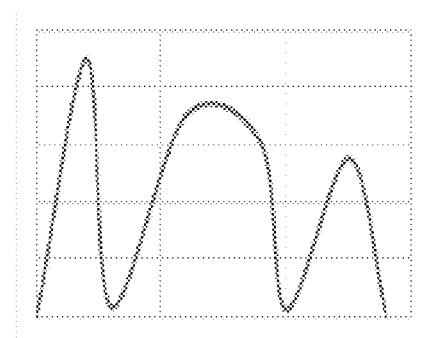

The clinical implication is the higher the mechanical interaction between the structures within the site the higher the internal/proximal mobility detected by the device described above. Additional site mobility is demonstrated in the Energy Return Curve or Energy Return Graph (ERG) by the shape of the curve (See FIG. 8). Specifically, the more structural pathology there is within the structure of the site (internal/proximal), the more the shape of the curve deviates from a uniform single peak. In addition, the software uses Levenberg-Marquardt algorithm to characterize the shape of the curve in terms of Normal Fit Error or NFE: higher NFE values are associated with greater additional mobility within the internal and/or proximal structure of tooth and/or implant. FIGS. 11, 11a, 11b and 11c illustrate generally characteristic ERG shapes that correspond to different levels of pathology. FIG. 11 shows a generally normal tooth with no structural pathology, FIG. 11a shows a generally mild level of pathology (as shown with the small additional peak), FIG. 11b shows a generally moderate level of pathology (as shown with the multiple small to medium peaks), and FIG. 11c shows a severe level of pathology (as shown with the large additional peaks).

Any of the devices described above may measure damping characteristics of an object, for example, a tooth or an implant. After application of kinetic energy to the object, the relative extent to which the object deforms inelastically and dampens elastic energy may be characterized as its loss coefficient, f, given by:

$$\eta = D/2\pi U$$

where D is the total energy dissipated (or lost) per unit volume and U is the elastic energy per unit volume. The clinical implication is the lower the loss coefficient value for the site, the more stable the tooth or implant is within the mandible. The overall site stability, and therefore the lack of overall mobility, is demonstrated the maximum amplitude of the ER response (See FIGS. 7 and 8). The higher this amplitude is, the lower the overall mobility that dissipates energy is and, therefore, the lower the loss coefficient.

The loss coefficient may be determined in the following manner using the formula stated above. The strain energy for any of the systems and methods discussed above is assumed to be approximately the same as the kinetic energy of the energy application tool, for example the tapping rod just prior to impacting the object. The energy dissipated (D) is defined as:

$$D = U - E\epsilon \cdot D_p$$

where $E\epsilon$ is the elastic strain energy conserved and Dp is the energy dissipated by sources external to the object. Upon impact, the elastic strain $E\epsilon$ is returned to the energy application tool, for example, the tapping rod in the form of a stress wave.

In general, any solid material may be capable of damping activity, i.e., dissipated mechanical energy. Damping capacity may be characterized by the loss coefficient, f, as discussed above. The factor $2\pi$ is present in the equation to normalize the value of f per radian, as testing is generally carried out under cyclic loading.

Prior to the test, the device may be calibrated. In order to calibrate a given device, the acceleration of the tapping rod 110 or 120 before and during impact is measured for model objects made with model materials with known characteristics. The statistical variation of the material measurements is determined, thus providing an assessment of the overall accuracy and precision of the method and instrumentation. The standard deviation of the data for each material is determined for the maximum strain energy returned from the object 112 and its loss coefficient. The elastic strain energy conserved is given by:

$$E\epsilon = CF^2$$

where the constant, C, varies inversely with the effective elastic modulus of the tapping rod 110 or 120 and the force, F, is proportional to both the mass of the tapping rod 110 or 120 and the maximum acceleration of the tapping rod 110 or 120 as a result of the stress wave created from the impact. The value of $D_p$ which represents the energy dissipated by sources external to the specimen 112 did not vary significantly with different material specimens since it primarily depends on the energy losses in the handpiece 100 or 104, not the specimen 112. Thus, it is reasonable to assume that $D_p$ is relatively constant for a given testing configuration and for a given tapping rod 110 or 120. To determine the values of C and $D_p$, it was useful to measure the elastic strain energy conserved for two model materials for model objects that have known loss coefficient values, $\eta_1$ and $\eta_2$. By substituting equations and rearranging terms, the value of C was then given by:

$$C = C_{1,2} = 2\pi U(\eta_1 - \eta_2)/F_1^2 - F_2^2$$

where the subscripts 1 and 2 referred to the first and second model materials respectively. A determination of the value of C for the given testing configuration and tapping rod 110 or 120 then resulted in a determination of the value of $D_p$ given by:

$$D_p = D_{p1,2} = U(1 - 2\pi\eta_{1,2}) - C\, F_{1,2}^2$$

for either of the two model materials, thus completing calibration.

As mentioned before, the present invention has application in the prediction of internal damage including microcracking and delamination in composite structures and other engineering materials. For example, a test specimen of practically any size and shape may be tested and its structural characteristics easily predicted, including where objects are located in locations that were difficult to access or where liquid couplants could not be used.

Figure 9:
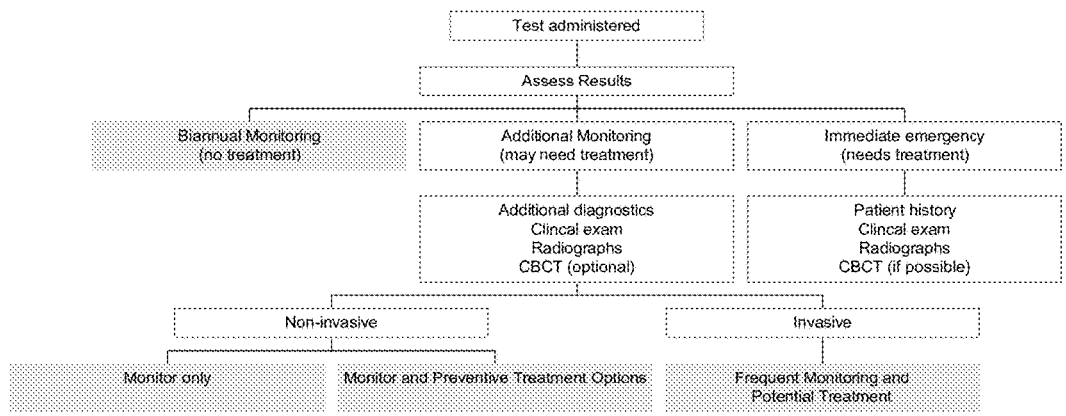
FIG. 9 illustrates a flow chart for utilizing data obtained from measurement of a tooth using the device and software of the present invention to indicate possible pathologies and treatment or monitoring options.

As noted above, computer modeling results may also be included in the predictive modeling to further enhance the model. For example, the simulation may be done on a system mimicking the above device and method, for example, at least one physical simulation model for at least one object configuration, for example, one tooth configuration may be included. The physical simulation model, for example, for a tooth, may be useful for simulating how at least one clinical finding may impact the test results from the device. In one embodiment, the physical simulation model may use an analysis, namely finite element analysis, to perform the simulation. In another embodiment, the default parameters for a physical simulation model, such as one based on finite element analysis, may be provided by a user. The process for establishing an initial physical simulation model may involve measurements and mathematical systems. FIG. 9 illustrates the use of the data obtained from testing teeth with the device(s) of the present invention, such as the handpiece 100 or 104, to assess whether any condition or issue is present and to recommend an appropriate follow-up action. When the results are assessed, such as by analysis of the damage and/or mobility values of the teeth obtained from the measurement, they may be compared to a set of previously obtained values which may be correlated to specific or general conditions of teeth, and the system may provide possible pathologies that may correspond to the damage and/or mobility values measured. For example, they may also be compared to generalized ERG results that indicate levels of pathology, as illustrated with the generalized ERGs representing normal, mild, moderate and severe levels of pathology as illustrated in FIGS. 11, 11a, 11b and 11c, respectively. In general, as illustrated at the third tier in FIG. 9, the assessment may return values consistent with: (1) no or low pathology, which may lead to generally recommend normal monitoring (e.g. biannual monitoring) and/or no further treatment; (2) medium concern for pathology, which may call for additional monitoring beyond normal, treatment, and/or additional diagnostics (e.g. clinical exams, radiographs, dental cone beam computerized tomography (CBCT), etc.) which may lead to either invasive or non-invasive follow-up options (e.g. monitoring and/or preventative treatment options for non-invasive and frequent monitoring and/or potential intervening treatment options for invasive); or (3) immediate or emergency concern for pathology, which may generally call for immediate additional diagnostics and treatment. In general, damage may be assessed for a value to detect structural instabilities, followed by analysis of the mobility value to determine the recommended actions, such as different treatment options, diagnostics, preventative actions, etc.

Figure 10:
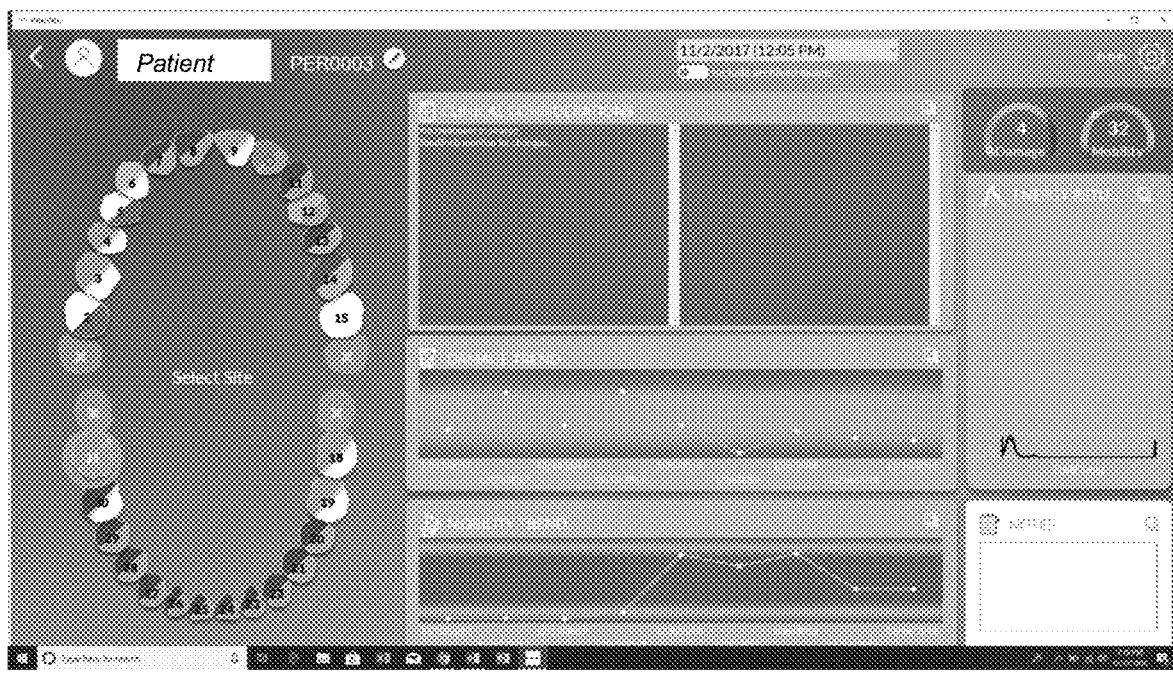
FIGS. 10 and 10a illustrate screenshots from monitoring software of the present software for showing the measurements over time for teeth of a patient.
Figure 10A:
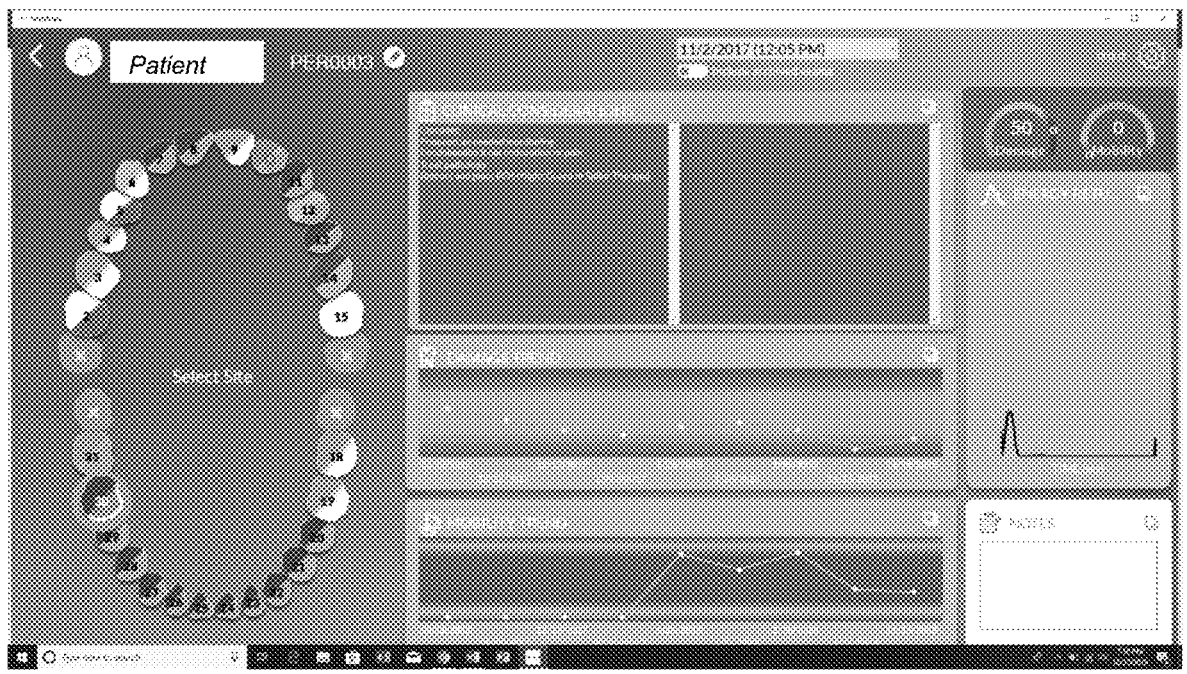

Data gathered from measurements using the devices of above, such as the handpiece 100 or 104, may also be recorded for particular teeth over time, such as at each monitoring session, such that trends in damage and mobility values may be monitored over time and may be used in overall treatment and/or monitoring planning. FIGS. 10 and 10a illustrate screenshots from measurement software (tooth 31 in FIG. 10 and tooth 30 in FIG. 10a being highlighted) where all of the teeth of a patient may be displayed (such as visually to give an overall snapshot view of all of the teeth) and individual records of monitoring over time may be displayed for each tooth for particularlized data about an individual tooth (such as the particular information for tooth 31 in FIG. 10 and for tooth 30 in FIG. 10a), including damage and/or mobility trends, clinical considerations, notes and the raw energy return curves.

Although the invention has been described with respect to specific aspects, embodiments and examples thereof, these are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

References throughout this specification to "one embodiment", "an embodiment", or "a specific embodiment" or similar terminology mean that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A system for predicting at least one structural characteristic of an object using a predictive model, comprising:
   a compilation of test results from a multitude of objects, each of said test results being generated by a device having a housing with an open end and a longitudinal axis comprising:
      an energy application tool mounted inside the housing for movement, said energy application tool having a resting and an active configuration;
      a sleeve protruding from the open end of the housing for a distance and having an object contacting portion at its open end adapted for resting said device on at least a portion of said object; and
      a drive mechanism supported inside the housing adapted for activating said energy application tool to impact said object when said object contacting portion of said sleeve is resting on at least a portion of said object and for measuring a response after impact and generating a response versus time curve, said response versus time curve having been annotated and validated;

a computer coupled to said device adapted for capturing any of said response, said response versus time curve and said annotation and validation to generate said predictive model having one or more characteristic ranges; and a transformation function adapted for identifying structural characteristics comprising a combination of loss coefficient and normal fit error from said predictive model;

wherein said predictive model is adapted for predicting said at least one structural characteristic of a newly tested object using said device with said transformation function when both said loss coefficient and said normal fit error in said combination fall into said one or more characteristic ranges without the need for further annotation and validation.

2. The system of claim 1 wherein said object comprises different objects or same objects at different time periods.

3. The system of claim 1 wherein said newly tested object comprises an object not tested before, or an object tested before at a different time period.

4. The system of claim 1, wherein said newly tested object is related to the objects already in the predictive model.

5. The system of claim 1, further comprising a program logic module executing a training cycle for training a machine learning algorithm on a ground truth dataset including stored device measurements and expert annotations to create said transformation function.

6. The system of claim 1 wherein said response versus time curve is annotated and validated by a technician, engineer or a clinician.

7. The system of claim 1, wherein said loss coefficient is defined as:

$$D/2\pi U$$

where D is the total energy dissipated (or lost) per unit volume and U is the elastic energy per unit volume.

8. The system of claim 1, wherein said normal fit error is defined as the cumulative error between a normalized measured data and a nonlinear regression fit of the equation below to the normalized measured data:

$$\overline{E}_r = \beta \sin^2(\gamma t) \exp\left[-\frac{(t-\phi)^2}{\psi}\right]$$

where t is time and $\beta$, $\gamma$, $\phi$, and $\psi$ are parameters that are determined via a nonlinear regression fit to measured data.

9. The system of claim 1 wherein said predictive model further comprises information collected from other tests not generated by the said device.

10. The system of claim 9 wherein said other tests for an anatomical object comprises results from computer modeling, radiography, transillumination, disassembling, examinations after extraction, or combinations thereof.

11. A computerized method for automatically determining structural characteristics of an object in a non-invasive manner and/or a non-destructive manner, comprising:

creating a predictive modeling by compiling test results from a multitude of objects, each of said test results being generated by a test procedure using a predictive modeling device having an energy application tool capable of applying energy to an object to generate a measurement to create a response versus time curve;

annotating and validating said response versus time curve;

capturing said response versus time curve and said annotation and validation to create said predictive model;

loading said model and said test procedure into a test device being substantially the same as said predictive modeling device;

instructing an operator to test a new object by using said test device on said new object and automatically generating a transformation function comprising a combination of loss coefficient and normal fit error from said model; and applying said transformation function to predict said at least one structural characteristic of said new object when both said loss coefficient and said normal fit error in said combination fall into said one or more characteristic ranges without operator participation.

12. The method of claim 11, further comprising executing a training cycle for training a machine learning algorithm on a ground truth dataset including captured device measurements of response versus time curve and said annotation and validation to create said transformation function.

13. The method of claim 11 wherein said instructing said operator comprises:

preparing the object;

locating a proper location for placing at least a portion of a sleeve of said test device on said object; and activating said test device and holding it steady for the duration of the test.

14. The method of claim 11 further comprising the addition of information collected from other tests not generated by the said test device into the predictive model.

15. The method of claim 11 wherein said device having a housing with an open end and a longitudinal axis:

a sleeve protruding from the open end of the housing for a distance and having an object contacting portion at its open end adapted for resting said device on at least a portion of said object; and a drive mechanism supported inside the housing adapted for activating said energy application tool to impact said object when said object contacting portion of said sleeve is resting on at least a portion of said object.

16. The method of claim 11 wherein said prediction further comprises predicting a further course of action for said test object.

17. A method for predicting at least one structural characteristic of an object using a predictive model, comprising:

generating test results from a multitude of objects, each of said test results being generated by a device having an energy application tool capable of applying energy to an object to generate measurement to create a response versus time curve;

annotating and validating said response versus time curve;

coupling a computer to said device for capturing said response versus time curve and said annotation and validation to generate said predictive model; and using a transformation function comprising a combination of loss coefficient and normal fit error from said predictive model to predict said at least one structural characteristic of a newly tested object using said device with said transformation function when both said loss coefficient and said fit error in said combination fall into said one or more characteristic ranges without the need for said annotation and validation.

18. The method of claim 17, wherein said device comprises:
- a housing with an open end and a longitudinal axis;
- a sleeve protruding from the open end of the housing for a distance and having an object contacting portion at its open end adapted for resting said device on at least a portion of said object; and
- a drive mechanism supported inside the housing adapted for activating said energy application tool to impact said object when said object contacting portion of said sleeve is resting on at least a portion of said object.

19. The method of claim 17 wherein said annotating and validating of said response versus time curve is performed by a technician, engineer or a clinician.

20. The method of claim 17 further comprising an interface for coupling to the computer for storing the measurement of the device, said response versus time curve and said annotation and validation.

* * * * *